United States Patent
Rock et al.

(10) Patent No.: US 8,597,664 B2
(45) Date of Patent: *Dec. 3, 2013

(54) ENDOGENOUS ADJUVANT MOLECULES AND USES THEREOF

(75) Inventors: Kenneth L. Rock, Chestnut Hill, MA (US); Yan Shi, Auburn, MA (US)

(73) Assignee: University of Massachusetts, Boston, MA (US)

( * ) Notice: Subject to any disclaimer, the term of this patent is extended or adjusted under 35 U.S.C. 154(b) by 72 days.

This patent is subject to a terminal disclaimer.

(21) Appl. No.: 12/879,471

(22) Filed: Sep. 10, 2010

(65) Prior Publication Data

US 2011/0123566 A1    May 26, 2011

Related U.S. Application Data

(63) Continuation of application No. 10/846,381, filed on May 13, 2004, now Pat. No. 7,807,187.

(60) Provisional application No. 60/470,396, filed on May 13, 2003.

(51) Int. Cl.
*A61K 39/00*  (2006.01)

(52) U.S. Cl.
USPC .................. 424/278.1; 424/184.1; 424/282.1; 424/204.1; 424/234.1

(58) Field of Classification Search
None
See application file for complete search history.

(56) References Cited

U.S. PATENT DOCUMENTS

| | | |
|---|---|---|
| 5,928,647 A | 7/1999 | Rock |
| 5,951,975 A | 9/1999 | Falo, Jr. et al. |
| 6,194,204 B1 | 2/2001 | Crawford et al. |
| 7,807,187 B2 * | 10/2010 | Rock et al. ................. 424/278.1 |
| 2002/0146396 A1 | 10/2002 | Albert et al. |

OTHER PUBLICATIONS

Shi et al., PNAS, 2000, vol. 97, p. 14590-14595.*
Shi et al., Eur J. Immunology, 2002, vol. 32, p. 155-162.*
Shi et al., 2003, Nature vol. 425, p. 516-521.*
Albert, Matthew L. et al, "Dendritic cells acquire antigen from apoptotic cells and induce class I-restricted CTLs," Nature, vol. 392:86-89 (1998).
Bosmansky, K. et al, "Serum uric acid levels in disorders of the rheumatic type," Z. Rheumatol., vol. 43(2):59-62 (1984).
Gallucci, Stefania et al, "Natural adjuvants: Endogenous activators of dendritic cells," Nature Medicine, vol. 5(11):1249-1255 (1999).
Hamilton, John A. et al, "Inflammatory microcrystals induce murine macrophage survival and DNA synthesis," Arthritis Res, vol. 3:242-246 (2001).
Hooper, D.C. et al, "Uric acid, a natural scavenger of peroxynitrite, in experimental allergic encephalomyelitis and multiple sclerosis," Proc. Natl. Acad. Sci. USA, vol. 95:675-680 (1998).
Janeway, Jr., Charles A., "The immune system evolved to discriminate infectious nonself from noninfectious self," Immunology Today, vol. 13(1):11-16 (1992).
Koka, Rima M. et al, "Adhesion of uric acid crystals to the surface of renal epithelial cells," Am J Physiol Renal Physiol, vol. 278:F989-F998 (2000).
Landis, R. Clive et al, "Safe Disposal of Inflammatory Monosodium Urate Monohydrate Crystals by Differentiated Macrophages," Arthritis & Rheumatism, vol. 46(11):3026-3033 (2002).
Matzinger, Polly, "Tolerance, Danger, and the Extended Family," Annu. Rev. Immunol., vol. 12:991-1045 (1994).
Matzinger, Polly, "An innate sense of danger," Seminars in Immunology, vol. 10:399-415 (1998).
Persing, David H. et al, "Taking toll: lipid A mimetics as adjuvants and immunomodulators," Trends in Microbiology, vol. 10(10 Suppl. )S32-S37 (2002).
Schumacher, Jr., H. Ralph, "Crystal-induced Arthritis: An Overview," The American Journal of Medicine, vol. 100(Suppl. 2A):46S-52S (1996).
Schumacher, Jr., H. Ralph et al, "Randomised double blind trial of etoricoxib and indometacin in treatment of acute gouty arthritis," BMJ, vol. 324:1488-1492 (2002).
The Merck Manual of Diagnosis and Therapy, "Crystal-Induced Conditions," Seventeenth Edition, Mark H. Beers (Ed.), Merck Research Laboratories, Whitehouse Station, New Jersey, pp. 460-463 (1999).
Yagnik, Darshna R. et al, "Noninflammatory Phagocytosis of Monosodium Urate Monohydrate Crystals by Mouse Macrophages," Arthritis & Rheumatism, vol. 43(8):1779-1789 (2000).
International Search Report Application No. PCT/US04/15214, 3 pages, dated Oct. 13, 2004.

* cited by examiner

*Primary Examiner* — Yunsoo Kim
(74) *Attorney, Agent, or Firm* — Nelson Mullins Riley & Scarborough LLP; Debra J. Milasincic, Esq.; Cynthia L. Kanik

(57) ABSTRACT

Methods of modulating the immune response using pharmaceutical compositions containing crystalline adjuvants are described. In various embodiments the crystalline adjuvants are selected from the group consisting of monosodium urate (MSU), xanthine, basic calcium phosphate (BCP), calcium pyrophosphate dihydrate (CPPD), hydroxyapatite, calcium oxalate, cholesterol, lipid liquid, other crystalline lipids, lithium heparin, talc, and starch.

16 Claims, 8 Drawing Sheets

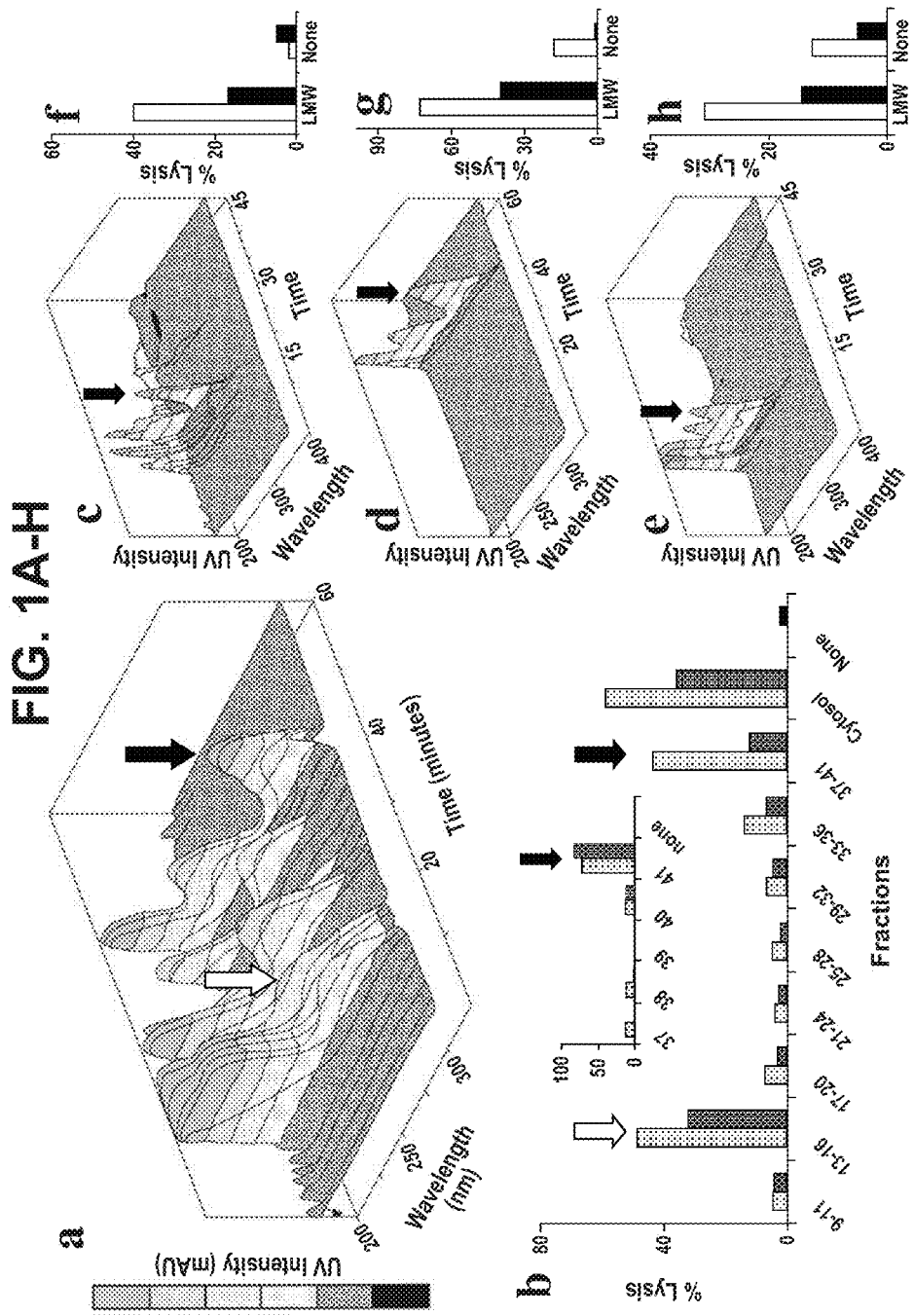

FIG. 2A-G
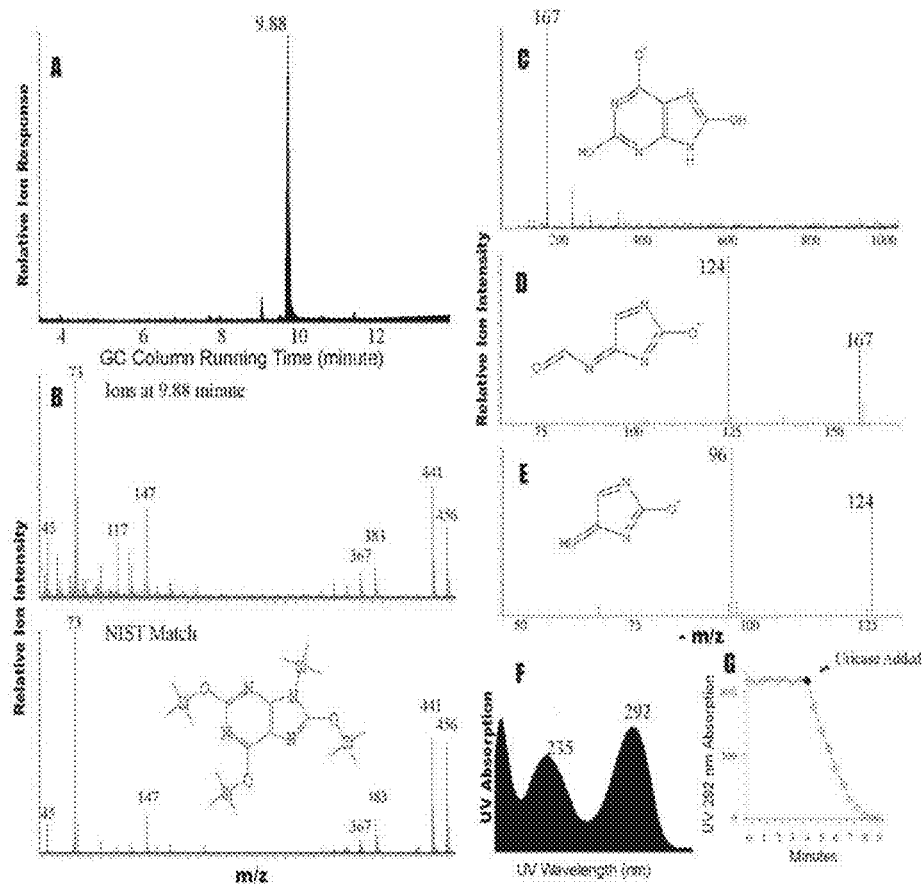

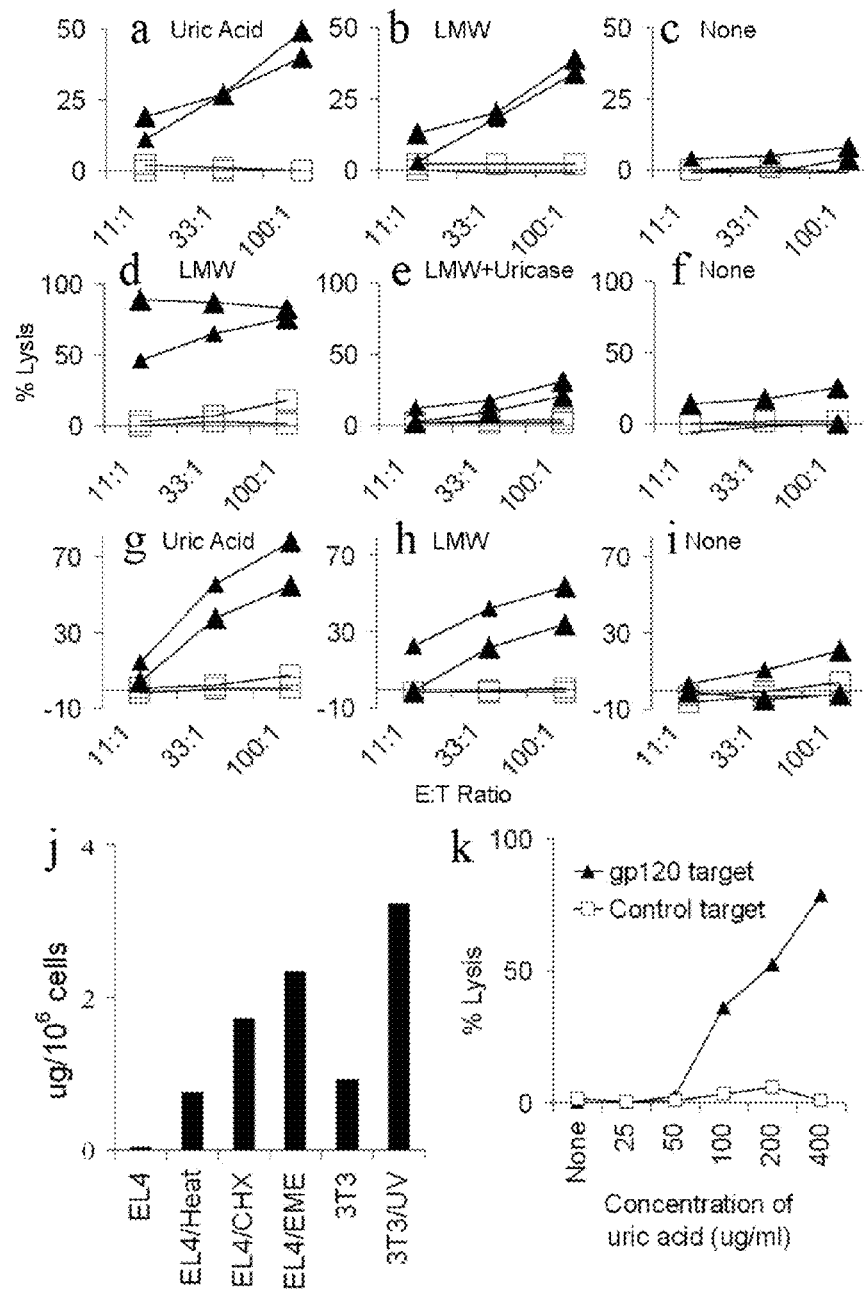
FIG. 3A-K

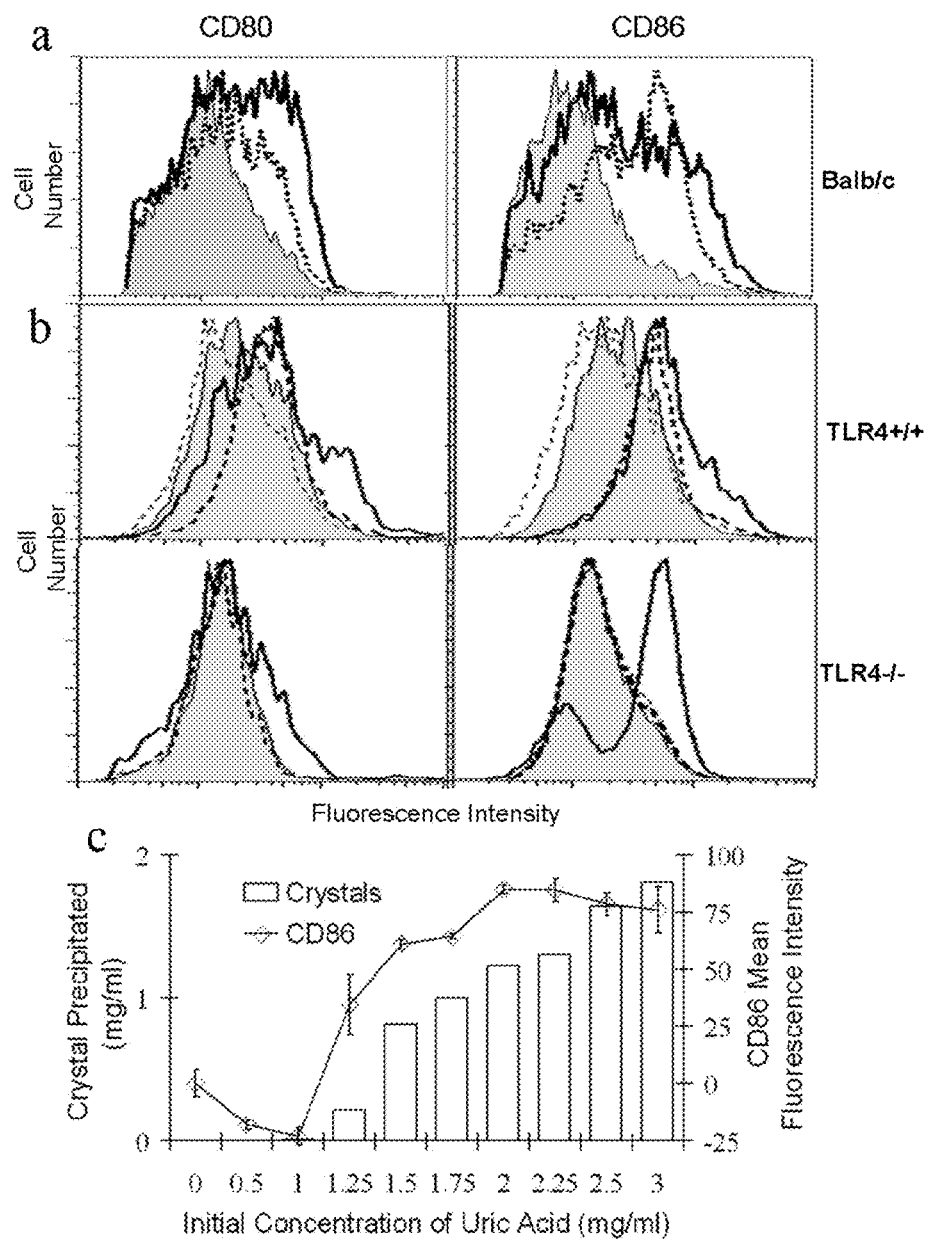
FIG. 4A-C

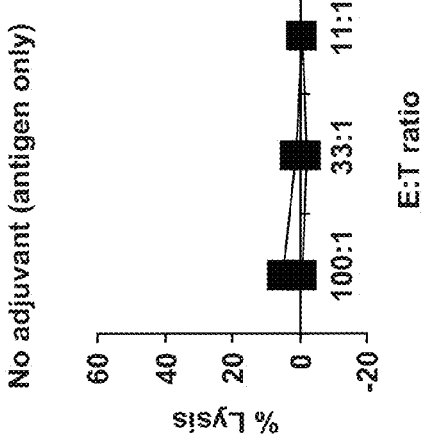
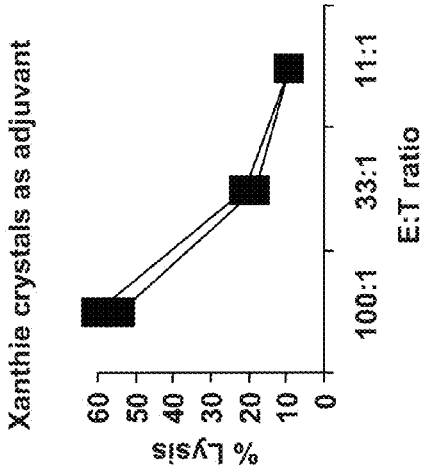
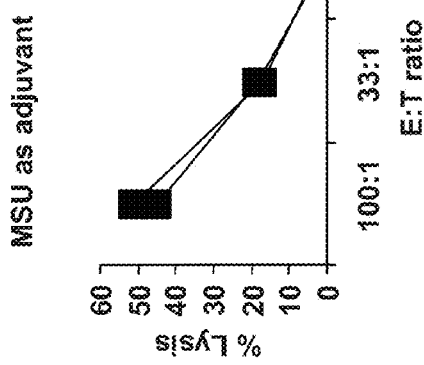

ENDOGENOUS ADJUVANT MOLECULES AND USES THEREOF

RELATED APPLICATIONS

This patent application claims the benefit of U.S. Provisional Patent Application Ser. No. 60/470,396, entitled "Endogenous Adjuvant Molecules and Uses Thereof", filed May 13, 2003. The entire contents of the above-referenced provisional patent application are incorporated herein by this reference.

GOVERNMENT RIGHTS AS TO FEDERALLY SPONSORED RESEARCH

This invention was made with Government support under grant nos. CA076341 and AI043543 awarded by the National Institutes of Health. The Government has certain rights in the invention.

FIELD OF THE INVENTION

The field of the invention is immune adjuvants, particularly endogenous adjuvants and their use in vaccines.

BACKGROUND OF THE INVENTION

For prophylaxis, it is essential that vaccines cause minimal morbidity. Live vaccines, including attenuated viruses or viral vectors, have the potential to cause disease, particularly in immuno-compromised individuals. For this reason, the ideal vaccines for prophylaxis contain nonliving components, termed subunit vaccines. One limitation of subunit immunizations is that they generally induce weaker and less long-lasting immunity than live vaccines, therein limiting their efficacy. Moreover, subunit vaccines do not effectively stimulate cytotoxic T lymphocytes (CTLs), cells which mediate one of the major immune responses that protects against viral infections. CTLs kill host cells that are infected by a virus and thereby eliminate the production and/or reservoir of virus. CTLs are critical components in the defense against several viruses including influenza, Pox and LCMV (4-6), as well as some parasites and bacteria. Given the important role of CTLs in host defense, there is a pressing need to develop vaccines that stimulate this arm of the immune system.

It has been known since the 1920's that immunization with a foreign protein by itself was often ineffective in stimulating immunity.[2] To generate immune responses the antigen needed to be admixed with other molecules that helped generate immunity. These molecules were termed adjuvants, from the Latin word "adjuvare", which means to help. Because many of the adjuvant molecules were derived from bacteria, this has been described as the "immunologist's dirty little secret".[3] Why adjuvants are required and how they work to promote immunity has become apparent only in recent years.

Currently there are only two adjuvants approved for use in man. One of these, Alum, functions only weakly and appears to induce preferentially TH2 immunity, a type of immunity which is inappropriate for many pathogens. While other adjuvants have been developed, approval for use in man has been elusive due to unacceptable side effects including inflammation and carcinogenicity. Accordingly, there is the need to develop new and better adjuvants.

Currently, the kinds of adjuvants that are available are formulations that create a depot of antigen and/or contain microbial components that help stimulate responses. There is some evidence that mammalian cells also produce their own adjuvants (termed "endogenous adjuvants" or "danger signals"), molecules that are released when the cells are injured and that help stimulate immune responses. However, to date, these endogenous adjuvants have not been isolated in a form that is useful for vaccines and their molecular identity is unknown. Therefore, elucidation of the molecular identity of these endogenous adjuvant molecule(s) is clearly needed as they could be highly useful as a novel class of adjuvants for vaccines.

SUMMARY OF THE INVENTION

The present invention is based on the unexpected discovery that uric acid is an endogenous immune adjuvant. When released from dying cells, uric acid stimulates dendritic cells to mature and augments the priming of T cell responses to antigen. In particular, monosodium urate (MSU) exhibit strong adjuvant activity. Similarly, xanthine displays adjuvant activity. Accordingly, the invention relates to compositions containing crystalline adjuvant molecules, e.g., uric acid (e.g., MSU crystals) or xanthine (e.g., xanthine crystals), their use to stimulate an antigen-specific immune response, e.g., T cell response, and their use in vaccines.

In one aspect, the invention provides a pharmaceutical composition capable of inducing activation of antigen-presenting cells, wherein the composition includes an effective amount of a crystalline adjuvant and an effective amount of an antigen in a pharmaceutically acceptable carrier.

In a related aspect, the invention provides a pharmaceutical composition capable of inducing an antigen-specific immune response, wherein the composition includes an effective amount of a crystalline adjuvant and an effective amount of an antigen in a pharmaceutically acceptable carrier.

In another aspect, the invention provides a method of eliciting an antigen-specific immune response in a subject by administering a crystalline adjuvant and an antigen in an amount sufficient to elicit an antigen-specific immune response.

In a related aspect, the invention provides a method of eliciting an antigen-specific immune response in a subject by administering to the subject an amount of antigen-presenting cells sufficient to induce an antigen-specific immune response, wherein the antigen-presenting cells have been contacted with a crystalline adjuvant and antigen in amounts sufficient to induce activation of the antigen-presenting cells.

In various embodiments of these aspects of the invention, the crystalline adjuvant comprises a crystal with a needle, rod or spherule morphology. In other embodiments, the crystal has a length of about 1-40 µm. In further embodiments, the crystal exhibits strong birefringeance and negative elongation. In still other embodiments, the crystal exhibits one or more of the above characteristics.

In certain embodiments, the crystalline adjuvant comprises a crystal selected from the group consisting of monosodium urate (MSU), xanthine, basic calcium phosphate (BCP), calcium pyrophosphate dihydrate (CPPD), hydroxyapatite, calcium oxalate, cholesterol, lipid liquid, other crystalline lipids, lithium heparin, talc, and starch. In certain preferred embodiments, the crystalline adjuvant comprises uric acid, and most preferably, the adjuvant comprises monosodium urate (MSU). In other preferred embodiments, the crystalline adjuvant comprises xanthine. Also preferably, the crystalline adjuvant is present in an amount sufficient to precipitate in vivo. For example, in preferred embodiments involving uric acid, the uric acid is administered such that the serum concentration is greater than about 70 µg/ml.

In other embodiments, the antigen-specific response elicited using the compositions and methods of the invention is a T cell response, e.g., a CD8+ T cell response and/or a CD4+ T cell response. In other embodiments, the antigen-specific immune response is an antibody response.

Antigens that can be used in the compositions and methods of the invention include, but are not limited to, a viral antigen, a tumor antigen, a bacterial antigen, a parasitic antigen, and a pathogenic self protein. In various embodiments, the antigen is a protein, peptide, carbohydrate, lipid, nucleic acid, or an inactivated virus or bacteria. In still other embodiments the antigen comprises a mixture of peptides, e.g., a mixture of peptide epitopes derived from the antigenic proteins of a pathogenic organism.

In still another aspect, the invention provides a method of activating an antigen-presenting cell, comprising contacting the antigen-presenting cell with an effective amount of a crystalline adjuvant and an effective amount of an antigen, such that the antigen-presenting cell is activated.

In a related aspect, the invention provides a method of generating antigen-specific T lymphocytes, comprising contacting antigen-presenting cells with a crystalline adjuvant and antigen in amounts sufficient to activate the antigen-presenting cells and contacting T lymphocyte precursors with the antigen-presenting cells for a sufficient time to induce the T lymphocyte precursors to become activated antigen-specific T lymphocytes.

In various embodiments of these aspects of the invention, the antigen-presenting cell is selected from the group consisting of a dendritic cell, mononuclear phagocyte, and B lymphocyte. In one preferred embodiment, the antigen-presenting cell is a dendritic cell. In other embodiments of this aspect of the invention, the T lymphocytes comprise CD4+ T lymphocytes and/or CD8+ T lymphocytes.

In one embodiment, the activation of the antigen-presenting cell is associated with presentation of antigen on the antigen-presenting cells. Alternatively, the activation is associated with increased expression of costimulatory molecules by antigen-presenting cells, e.g., CD80 or CD86. In other embodiments, the method involves contacting the antigen-presenting cell with an effective amount of the adjuvant and antigen ex vivo. In alternative embodiments, the method involves contacting said antigen-presenting cell with an effective amount of uric acid and an effective amount of an antigen occurs in vivo. In yet other embodiments, the antigen-specific T lymphocytes are administered to an individual afflicted with a disease. Alternatively, the antigen-specific T lymphocytes are administered to an individual at risk of developing a disease.

In still another aspect, the invention provides a kit including an effective amount of crystalline adjuvant and an effective amount of an antigen, and wherein the kit further comprises instructions for use.

In still another aspect, the instant invention provides a method of reducing an undesired immune response in a subject involving administering a substance capable of reducing uric acid concentration in an amount sufficient to reduce the concentration of uric acid, such that the undesired immune response is reduced.

In a related aspect, the invention provides a method of reducing inflammation in a subject suffering from an inflammatory condition involving administering a substance capable of reducing uric acid concentration in an amount sufficient to reduce the concentration of uric acid, wherein the uric acid level in the serum of the subject is below about 70 μg/ml, such that the inflammation is reduced.

In one embodiment of this aspect of the invention, the serum uric acid level in the subject is between about 18 and about 65 μg/ml. Preferably, the serum uric acid level in the subject is between about 40 and about 60 μg/ml. In one embodiment, the subject further has an elevated uric acid concentration at the site of inflammation. In various other embodiments, the inflammatory condition is selected from the group consisting of tissue injury, wound, myocardial infarction, post-surgical wounds, and post-trauma. In one embodiment, the inflammatory condition is associated with injured or dying cells.

In still another aspect, the invention provides a method for identifying an agent useful for reducing inflammation associated with cell injury involving contacting an apoptotic cell with a test agent and assaying for an indicator of uric acid production, whereby an agent is identified based on its ability to reduce uric acid produced by said apoptotic cell in comparison to a suitable control.

In yet another aspect, a method is provided for inducing in a subject at risk of exposure to a pathogen an increased non-specific resistance to the pathogen involving administering a crystalline adjuvant in an amount sufficient to increase non-specific resistance.

In various embodiments of this aspect of the invention, the crystalline adjuvant comprises a crystal with a needle, rod or spherule morphology. In other embodiments, the crystal has a length of about 1-40 μm. In further embodiments, the crystal exhibits strong birefringeance and negative elongation. In still other embodiments, the crystal exhibits one or more of the above characteristics. In certain embodiments, the crystalline adjuvant comprises a crystal selected from the group consisting of monosodium urate (MSU), xanthine, basic calcium phosphate (BCP), calcium pyrophosphate dihydrate (CPPD), hydroxyapatite, calcium oxalate, cholesterol, lipid liquid, other crystalline lipids, lithium heparin, talc, and starch. In certain preferred embodiments, the crystalline adjuvant comprises uric acid, and most preferably, the adjuvant comprises monosodium urate (MSU). In other preferred embodiments, the crystalline adjuvant comprises xanthine.

BRIEF DESCRIPTION OF THE FIGURES

FIGS. 1A-1I are spectra and bar graphs depicting the purification of the LMW endogenous adjuvant from cytosol. FIG. 1A shows the UV-spectrum of 3T3 cytosolic fractions from a GF250 sizing column. FIG. 1B presents the anti-HIVgp120-specific CTL activity from Balb/c mice injected 14 days earlier with HIV-gp120 antigen beads alone (none), or admixed with either unfractionated cytosol or pooled fractions from A. Light grey and dark grey bars indicate % specific lysis induced by CTL tested at effector: target ratios of 100:1 and 33:1, respectively. The arrows show LMW active fractions and HMW active fractions in both A & B. The inset shows the same analysis except LMW fractions 37-41 were tested individually. FIGS. 1C, 1D and 1E show UV spectra of further and sequential purification of LMW fractions with adjuvant activity (arrows) on anion exchange, sizing, and reverse phase columns, respectively. FIGS. 1F, 1G and 1H present CTL activity from mice injected with HIVgp120 and the active LMW fractions (arrows) from FIGS. 1C, 1D and 1E, respectively. FIG. 1I shows the UV-spectra of 3T3 cytosolic fractions (upper panel) and liver cytosolic fractions (bottom panel) from a Superdex 75 HR 10/30 sizing column.

FIGS. 2A-2G are spectra and graphs depicting the molecular identification of the LMW endogenous adjuvant. FIG. 2A shows the total ion current plot from GC-EIMS analysis of a TMS-derivatized LMW active fraction purified by HPLC sequentially on sizing, ion exchange, second sizing and reverse phase columns. The top panel of FIG. 2B depicts a full electron impact mass spectrum of the component eluting at 9.88 minute from FIG. 2A, while the bottom panel depicts the matching mass spectrum from the NIST database and, in the insert, the structure (tetra-TMS uric acid). FIG. 2C shows the infusion negative ion ESI ion trap MS spectrum of the active LMW C18 column fraction as purified in FIG. 1E. FIG. 2D and FIG. 2E show the $MS^2$ and $MS^3$ product ion spectra of m/z 167 and m/z 124 ions from FIGS. 2C and 2D, respectively, and the insets are proposed product ion structures. FIG. 2F shows the UV spectrum of a uric acid standard at neutral pH. FIG. 2G is a graph depicting uricase degradation of the highly purified LMW fraction as indicated by the reduction of UV absorption at 292 nm measured with a photo-spectrometer.

FIG. 3A-3K are graphs demonstrating that uric acid has adjuvant activity in vivo. In FIGS. 3A, 3B and 3C, highly purified uric acid (50 μg), highly purified LMW fraction from a C18 column, or PBS, respectively, were mixed with 5 μg gp120/latex beads in 100 μl of saline and injected into two Balb/c mice. CTL from these mice were assayed for killing of 15.12 (gp120-transfected 3T3) cells (filled triangles), or vector-transfected control 3T3 cells (open squares). Results from individual mice are presented. FIGS. 3D, 3E and 3F depict results from experiments similar to those of FIGS. 3A-3C except that control-treated and uricase-treated LMW fractions were used in place of uric acid and untreated LMW fractions, respectively. FIGS. 3G, 3H and 3I depict results from experiments similar to FIGS. 3A-C except that congenic C.C3H lps-d (TLR4−/−) mice were used in place of Balb/c (TLR4+/+) mice. FIG. 3J is a bar graph showing that levels of uric acid increase in injured cells. EL4 cells were either heat shocked for 20 minutes at 45° C., incubated with 25 μg/ml cycloheximide or 8 μM emetine, or untreated as control. 3T3 cells were either untreated or UV-irradiated. After 5 hours the amount of uric acid in the cytosol of the treated cells was determined. FIG. 3K depicts results from an experiment in which 100 μl of uric acid solution (in pH 8.5 0.1 N borate) at indicated concentrations was injected together with antigen into mice and the CTL from the mice were then assayed for killing as described in FIGS. 3A-C. The values are the average percentage lysis (100:1 ET ratio) of targets by CTL from two mice.

FIG. 4A-B are graphs depicting expression of CD80 and CD86 on dendritic cells following exposure to MSU crystals and demonstrating that MSU crystals rapidly activate dendritic cells in vitro. In FIG. 4A, bone marrow-derived dendritic cells from Balb/c mice were untreated (thin continuous line) or incubated with 20 μl of pre-formed MSU crystals for 6 hours (heavy dashed lines) or 24 hours (heavy continuous lines). The expression of CD80 and CD86 on CD11c+ cells was then analyzed by flow cytometry. In FIG. 4B, dendritic cells from C57BL/6 (TLR4+/+) or C.C3H lps-d (TLR4−/−) mice were untreated (thin continuous lines) or incubated for 6 hours with uric acid (70 μg/ml, a concentration at which crystals do not precipitate within 6 hours, thin dashed lines), 1 μg/ml LPS (heavy dashed lines), or 20 μl pre-formed MSU crystals (1.2 mg/ml final concentration) (heavy continuous lines). The expression of CD80 and CD86 on the dendritic cells was then similarly analyzed.

FIG. 4C depicts the correlation between formation of MSU crystals and activation of dendritic cells. Uric acid at indicated concentrations was added to Balb/c dendritic cell culture and incubated for 24 hours. The expression of CD86 (diamonds) was analyzed as in FIG. 4A. The quantities of precipitated crystals (open bars) were determined as described in the Materials and Methods of the Examples.

FIG. 7A-7C are graphs demonstrating that xanthine has adjuvant activity in vivo. In FIGS. 7A, 7B and 7C, highly purified MSU crystals (500 μg), highly purified xanthine crystals (500 μg), or PBS, respectively, were mixed with 2 μg gp120/latex beads in 100 μl of saline and injected into two Balb/c mice. CTL from these mice were assayed for killing of 15.12 (gp120-transfected 3T3) cells (filled squares). Results from individual mice are presented.

DETAILED DESCRIPTION OF THE INVENTION

Figure 1I:
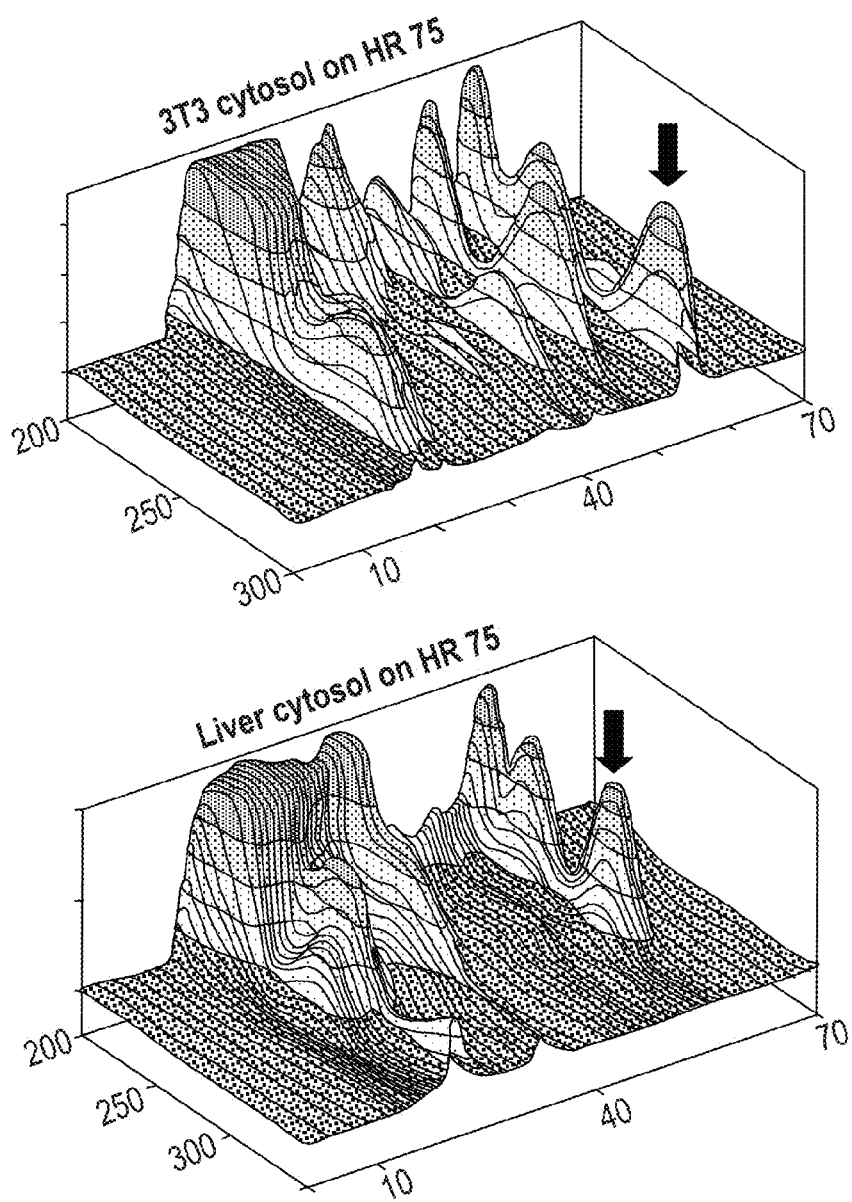

The immune system needs to detect foreign antigens present in any location in the body. It accomplishes this function by deploying in all tissues sentinel cells that sample the antigens in the local environment and then migrate to secondary lymphoid organs to report the information they have acquired to lymphocytes. The sentinel cells are generically referred to as antigen presenting cells (APC), the most important of which are dendritic cells.[1] In the tissues, dendritic cells are in an "immature" state where they avidly acquire antigens from the environment but have a limited capability to present these antigens and stimulate T cells.[1,4] Thus, they have high rates of endocytosis and are phagocytic, but present antigen poorly and express few costimulatory molecules. After acquiring antigen the APC migrate from the tissues to lymphoid organs. During this process the APC "mature", decreasing their rates of endocytosis and upregulating their ability to present antigens and costimulate T cells.[1,4] Migration and maturation of the APC can be stimulated by microbial products, such as LPS, and these effects are believed to be the basis for how many adjuvants promote immunity.[5,6] The microbial products mediate these effects by stimulating receptors on APCs, the best characterized of which are toll-like receptors that recognize pathogen-associated molecular patterns.[7,8] In the absence of such activating stimuli, the APC remain immature and/or are less stimulatory and in this state may lead to non-responsiveness or even tolerance to an antigen.[9]

These and other findings have led to the concept that the immune system responds not simply to foreign antigen, but to antigen that is in the context of a dangerous situation for the host, such as an infection.[10,11] By this model, microbial adjuvants provide the danger signal that promotes generation of immunity during infections or to vaccines. In the case of tumors or microbes that lack associated adjuvants, however, it is unclear what provides this danger signal. In these situations it has been hypothesized that injured and dying cells might release an endogenous danger signal.[10,12] Supporting this hypothesis, dying cells have been observed to activate dendritic cells in vitro and in vivo.[13,14] Moreover, when dying cells were co-injected with antigen into animals, they provided an adjuvant effect for priming T cell responses.[15,16] This endogenous adjuvant activity was present in the cell cytosol and increased significantly when cells were injured. However, while novel adjuvants for vaccines are clearly needed in the art, the clinical use of whole cells or crude cell lysates as an adjuvant for clinically useful vaccines in man would not be practical or safe. Prior to the discovery set forth herein, the molecular identity of this endogenous danger signal(s) in injured cells was not known.

The present invention is based on the unexpected discovery that uric acid is effective as an immune adjuvant. The instant inventors have demonstrated that uric acid, when released from dying cells, stimulates dendritic cells to mature and augments the priming of T cell responses to antigen. The instant inventors further demonstrated that the ability of uric acid to stimulate maturation of dendritic cells correlates with the extent of precipitation of uric acid to MSU crystals. Moreover, xanthine was similarly found to exhibit adjuvant activity. Accordingly, the invention relates to compositions containing crystalline adjuvant and their use in vaccines to elicit an antigen-specific immune response in a subject. Methods of activating antigen-presenting cells and generating antigen-specific T lymphocytes are also provided.

I. Definitions

As used herein, each of the following terms has the meaning set forth below.

The articles "a" and "an" are used herein to refer to one or to more than one (i.e., at least one) of the grammatical object of the article. By way of example, "an element" means one element or more than one element.

"Acute inflammation" is associated with disorders in which tissue inflammation is generally of relatively short duration, and lasts from about a few minutes to about one to two days, although it may last several weeks. The main characteristics of acute inflammatory disorders include increased blood flow, exudation of fluid and plasma proteins (edema) and emigration of leukocytes, such as neutrophils.

A "crystalline adjuvant" as used herein refers to an adjuvant that is composed of molecules that form crystals at saturated concentrations. The crystalline adjuvant can contain the molecules in a soluble form, which upon entry into the body, are capable of forming crystals upon deposition in the tissues. Alternatively, the crystalline adjuvant can contain the molecules in crystalline form, e.g., as a suspension.

Unless otherwise specified herewithin, the terms "antibody" and "antibodies" broadly encompass naturally-occurring forms of antibodies (e.g., IgG, IgA, IgM, IgE) and recombinant antibodies such as single-chain antibodies, chimeric and humanized antibodies and multi-specific antibodies, as well as fragments and derivatives of the foregoing, which fragments and derivatives have at least an antigenic binding site. Antibody derivatives can further comprise a protein or chemical moiety conjugated to an antibody moiety.

"Cancer" includes a malignant neoplasm characterized by deregulated or uncontrolled cell growth. The term "cancer" includes benign neoplasms, primary malignant tumors (e.g., those whose cells have not migrated to sites in the subject's body other than the site of the original tumor) and secondary malignant tumors (e.g., those arising from metastasis, the migration of tumor cells to secondary sites that are different from the site of the original tumor). As used herein, the term "tumor" is intended to encompass both in vitro and in vivo tumors that form in any organ of the body. Tumors may be associated with benign abnormal cell growth (e.g., benign tumors) or malignant cell growth (e.g., malignant tumors).

A "kit" is any manufacture (e.g., package or container) comprising at least one reagent, e.g., uric acid or xanthine), for use as an immune adjuvant in the methods of the invention. The kit can be promoted, distributed or sold as a unit for performing the methods of the invention.

"Patient" or "subject" includes living multicellular organisms, preferably mammals. The term "mammals" of the invention includes all vertebrates, e.g., such as nonhuman primates, sheep, dog, cat, horse, and cows. Examples of subjects include humans, dogs, cows, horses, kangaroos, pigs, sheep, goats, cats, mice, rabbits, rats, mice, hamsters and transgenic non-human animals. In preferred embodiments, the patient or subject is a human. In particular embodiments, the patient or subject is a human patient with an inflammation or autoimmune disorder.

As used herein, the term "antigen-presenting cell" is intended to include all immune cells capable of presenting an antigen to the immune system (e.g., on the cell surface), including dendritic cells, mononuclear phagocytes, B lymphocytes, and the like, from a mammal (e.g., human or mouse).

As used herein, the term "macrophage" is intended to include all cells within the macrophage lineage, including monocytes, circulating macrophages, tissue macrophages, activated macrophages, and the like, from a mammal (e.g., human or mouse).

As used herein, the terms "CD86" and "CD80", also referred to as "B7-1" and "B7-2", respectively, refer to costimulators expressed preferentially by activated, e.g. mature, antigen-presenting cells and which provide secondary signals for activation of T lymphocytes.

As used herein, the term "activating an antigen-presenting cell" refers to inducing the maturation of an antigen-presenting cell such that it becomes immunostimulatory.

As used herein, the term "T cell" or "T lymphocyte" is intended to include all cells within the T cell lineage, including thymocytes, immature T cells, mature T cells and the like, from a mammal (e.g., human or mouse). "Helper T cell" or "helper T lymphocyte" refers to CD4+ T lymphocytes. "Cytotoxic T cell" or "cytotoxic T lymphocyte" or "CTL" refers to CD8+ T lymphocytes.

As used herein, the term "eliciting an antigen-specific immune response" refers to inducing a T lymphocyte response to an antigen, e.g., from a population of cells comprising a naive population of lymphocytes (i.e., a population of T lymphocytes that has not previously been exposed to the antigen) or from a population of cells comprising a population of memory T lymphocytes (i.e., a population of T lymphocytes previously activated by the antigen).

As used herein, the term "antigen" or "immunogen" means all, or parts thereof, of a molecule or organism capable of causing an immune response in a vertebrate, preferably a mammal. As used herein, an antigen or immunogen can be, e.g., subunit vaccines, proteins, peptides, carbohydrates, lipids, nucleic acids, whole live or attenuated organisms, or altered pathogens. Antigens can also be reactive with antibodies from animals immunized with an antigen. The potent accessory function of dendritic cells provides for an antigen presentation system for virtually any antigenic epitope which T lymphocytes are capable of recognizing through their specific receptors.

The words "polypeptide" and "peptide" are used interchangeably and designate a linear sequence of amino acids connected one to the other by peptide bonds between the alpha amino and carboxyl groups of adjacent amino acids. The peptides can be of a variety of lengths, either in their neutral (uncharged) form or in forms such as their salts and either free of modifications such as glycosylations, side chain oxidation or phosphorylation or containing such modifications. Also included in the definition are peptides modified by additional substituents attached to the amino side chains, such as glycosyl units, lipids or inorganic ions such as phosphates as well as chemical modifications of the chains. Thus, the term "peptide" or its equivalent is intended to include the appropriate amino acid sequence referenced, subject to the foregoing modifications, which do not destroy its functionality.

As used herein, the term "contacting" (i.e., contacting a cell with antigen and crystalline adjuvant, e.g., uric acid or xanthine) is intended to include incubating the antigen and crystalline adjuvant and the cell together in vitro (e.g., adding the antigen and crystalline adjuvant to cells in culture) and administering the antigen and crystalline adjuvant to a subject such that the antigen and crystalline adjuvant and cells of the subject are contacted in vivo.

The term "treatment" or "treating" as used herein refers to either (1) the prevention of a disease (prophylaxis), or (2) the reduction or elimination of symptoms of the disease of interest (therapy).

The terms "prevention", "prevent" or "preventing" as used herein refers to inhibiting, averting or obviating the onset or progression of a disease (prophylaxis).

As used herein, the terms "immune" and "immunity" refers to the quality or condition of being able to resist a particular disease.

The terms "immunize" and "immunization," as used herein, refer to the act of making a subject (1) not susceptible to a disease; or (2) less responsive to a disease; or (3) have an increased degree of resistance to a disease.

As used herein, an "effective amount" of a crystalline adjuvant of the invention and/or antigen refers to an amount of crystalline adjuvant and/or antigen which is effective, either alone or in combination with a pharmaceutically acceptable carrier, and upon single- or multiple-dose administration to cells, at activating antigen-presenting cells or generating antigen-specific T lymphocytes.

As used herein, a "pharmaceutical composition" refers to a composition comprising an crystalline adjuvant, (e.g. uric acid or xanthine), and/or an antigen and a pharmaceutically acceptable carrier. Preferably, the pharmaceutical composition is sterile.

As used herein, a "pathogenic self protein" refers to a protein, typically an abnormal protein, which causes a disease, e.g., amyloid protein, which causes Alzheimer's disease.

II. Adjuvants

According to the methods of the instant invention, certain crystalline molecules can be used as an adjuvant to enhance a subject's immune response to an antigen. In one embodiment, exemplary molecules of the invention that can function as immune adjuvants are molecules that form crystals having similar characteristics to MSU crystals. Standard characteristics of MSU crystals include a needle, rod or spherule morphology. Typically, MSU crystals are submicroscopic, having a length of about 1-40 µm, and more usually 2-20 µm. MSU crystals exhibit a strong birefringeance, negative elongation with sharp extinction on the axis. Accordingly, in preferred embodiments of the instant invention, crystals useful as adjuvants have similar morphology, e.g. needle, rod or spherule, and size, e.g. submicroscopic, preferably about 1-40 µm, to MSU crystals. In other embodiments, crystals useful as adjuvants have similar morphology and size to other crystals, such as, for example, xanthine crystals. Preferred crystals for use as immune adjuvants in the instant invention include MSU, xanthine, CPPD and BCP. In one embodiment, a molecule useful as an adjuvant is a crystal formed by uric acid, e.g., a MSU crystal. In one embodiment, a molecule useful as an adjuvant is a crystal formed by xanthine. In other embodiments, molecules useful as adjuvants are modified forms, e.g., chemically modified forms, of uric acid or xanthine that retain the adjuvant activity of uric acid or xanthine as described herein. In one embodiment, chemically modified forms of uric acid useful in the instant invention retain the characteristics of a MSU crystal, e.g., characteristics such as a needle, rod or spherule morphology, and a submicroscopic size of length of about 1-40 µm. Chemically modified forms of uric acid or xanthine useful in the present invention are those commonly known in the art. It will be further understood by one of ordinary skill in the art that useful chemically modified forms of uric acid or xanthine can be identified in screening assays using the methods described herein to test for adjuvant activity.

Nonlimiting examples of other crystals that can be used as immune adjuvants include: basic calcium phosphate (BCP), calcium pyrophosphate dihydrate (CPPD), hydroxyapatite, calcium oxalate, cholesterol, lipid liquid, other crystalline lipids, lithium heparin, and talc (magnesium silicate) or starch crystals. Examples of yet other crystals that can be used as immune adjuvants include: cryoprotein crystals, lysophospholipase (Charcot-Leyden crystals), amyloid, ochronotic chards, hemoglobin, hematoidin, collagen fibrils, silicone, aluminum, cystine, xanthine and hypoxanthine crystals. Also within the scope of the instant invention is the use of synthetic crystals as immune adjuvants. It will be understood by one of ordinary skill in the art that the optimal dosage ranges of other crystals for stimulating an antigen-specific T lymphocyte response can be determined by using methods similar to those described herein for uric acid.

In certain embodiments, the crystalline adjuvant can be administered alone in order to enhance general immunity in a subject, e.g., to induce a heightened non-specific resistance to a pathogen in a subject, e.g., a subject at high risk of exposure to a pathogen or a subject that is immunocompromised. Subjects at high risk of infection include subjects having decreased neutrophil count (Prentice and Grob (1986) Clin. Hematol. 15:755-80). Also within the scope of the instant invention, crystalline adjuvant can be administered alone to modulate, e.g. down-modulate, the intensity of an immune response to endotoxin in a subject. The ability of a crystalline adjuvant to modulate a response to endotoxin, e.g., septic shock, can be assessed by monitoring clinical manifestations commonly known to be associated with endotoxin response, e.g. decreased blood pressure. For example, hymodynamic effects of lethal endotoxemia can be monitored by measuring hemodynamic parameters, e.g., arterial pressure, thermodilution cardiac output, and colloid osmotic pressure. Further methods of assessing the ability of crystalline adjuvants of the instant invention to enhance immunologic responsiveness or to induce a state of early endotoxin tolerance are known in the art, e.g., see: Madonna et al. (1986) Infect. Immun. 52:6-11; Welty and Ulrich (1989) Abstracts of the 89th Annual Meeting of the American Society for Microbiology, 31.

In other embodiments, the crystalline adjuvant is administered in combination with exogenous antigen, e.g., protein, carbohydrate, lipid, nucleic acid, or whole live or attenuated organism, to stimulate an antigen-specific T lymphocyte response, e.g. a CTL response. Preferably, the antigen mimics epitopes of a pathogenic organism or malignant disorder against which protection is sought. It is also within the scope of the instant invention that the crystalline adjuvant can be physically associated with the antigen, e.g., covalently or noncovalently associated with the antigen. When crystalline adjuvant and antigen are physically associated, the antigen and adjuvant are thereby delivered in particulate form. The crystalline adjuvant can be physically associated to an antigen according to methods well known in the art.

In preferred embodiments, antigen-presenting cells are contacted with the antigen and the crystalline adjuvant (e.g., uric acid or xanthine) such the crystalline adjuvant is present at the time of pulsing the antigen-presenting cells with the antigen. When administered in effective amounts in the presence of uric acid, the antigen is capable of activating antigen-presenting cells and generating antigen-specific T lymphocytes, and thereby is capable of eliciting an antigen-specific immune response.

Crystals useful in the adjuvants of the invention can be obtained from commercial sources or purified using methods well known to those skilled in the art. For example, uric acid used in certain preferred embodiments of the invention can be purified, e.g., according to methods set forth in the Examples, from a variety of sources, including, for example, human, murine, bovine, equine or other mammalian cells, and, e.g., from serum or body fluids normally containing uric acid. Mixtures of uric acid from these sources can also be used. Uric acid can be chemically synthesized according to standard methods commonly known in the art. Uric acid can be obtained from commercial sources, for example, from Sigma Chemical Co., St. Louis, Mo. (e.g. catalog no. U-0881). Monosodium urate (MSU) monohydrate crystals can be prepared from a supersaturated uric acid solution in pH 8.5 0.1 M borate, as described herein. MSU monohydrate crystals can also be prepared from twice-recrystallized uric acid and sodium hydroxide according to methods known in the art (e.g., see H. S. Cheung et al., (1984) *Arthritis Rheum* 27:668-674).

While not wishing to be bound by theory, it appears that the normal, endogenous concentration of crystalline compounds in extracellular mammalian body fluids which are useful as adjuvants is such that their ability to function as an adjuvant is limited. Thus, for in vivo applications, the amount of crystalline adjuvant (e.g., uric acid) administered to the host must be sufficient to increase the concentration of crystalline adjuvant (e.g., uric acid or xanthine) in the extracellular body fluids above the level normally present, for example, in mammalian serum, in order to stimulate an antigen-specific immune response (e.g., a CTL response). For ex vivo applications, the amount of crystalline adjuvant (e.g., uric acid or xanthine) that is contacted with antigen-presenting cells must be sufficient to activate the antigen-presenting cells or generate antigen-specific T lymphocytes.

Normal ranges of the concentration of any crystalline composition in mammalian serum and other extracellular fluids are readily ascertainable and in many instances are available in the published literature. For example, in adult humans, normal serum levels of uric acid can range from about 20-90 µg/ml, and normally are about 40-60 µg/ml (W. M. Mikkelsen et al., (1965) *Am. J. Med.* 39:242-251). Accordingly, precise amounts of any crystalline adjuvant can be tailored to the particular individual and to the particular application and antigens used in the immunization. Based on discoveries of the instant invention, it is expected that greater activation of antigen-presenting cells and greater induction of a T lymphocyte response will occur at higher concentrations of crystalline adjuvant. For example, in certain embodiments, the adjuvant comprises the crystalline molecules at a concentration sufficient to precipitate in vivo, e.g. to form crystals. In certain preferred embodiments, the adjuvant is uric acid, preferably, monosodium urate crystals. In other preferred embodiments, the adjuvant is xanthine, preferably xanthine crystals. In these preferred embodiments, the cells can be contacted with the crystalline adjuvant at concentrations greater than 5 µg/ml, 10 µg/ml, 20 µg/ml, 25 µg/ml, 30 µg/ml, 40 µg/ml, preferably greater than 50 µg/ml, more preferably greater than 60 µg/ml and still more preferably greater than 70 µg/ml. In one embodiment of the invention, cells are contacted with crystalline adjuvant in insoluble form, e.g. with MSU crystals or xanthine crystals. Crystals of the invention can have a diameter of about 0.1-300 µm, 0.2-200 µm, preferably about 0.5-100 µm, more preferably about 1-50 µm, and even more preferably about 2-30 µm.

The concentration of crystalline molecules used as adjuvants can be elevated systemically, i.e, throughout the body by increased levels in the blood. The concentration of crystalline molecules used as adjuvants can be elevated locally at the site of injection. The latter is more attractive clinically and economically, and hence is preferred. While the amount of crystalline adjuvant required to stimulate an antigen-specific T lymphocyte immune response may vary to some degree depending upon the exogenous antigen for which the immune response is desired and the mammal to be immunized, the determination of the optimal amount of crystalline adjuvant for a given vaccination protocol is within the skill of the art.

Optimal dosages of crystalline adjuvant for stimulating an immune response can be determined according to methods known in the art. For example, to determine the optimal dosages of crystalline adjuvant required for stimulating a T lymphocyte response to an antigen, e.g. protein(s), in a human being, human patients are immunized with differing dosages of protein and crystalline adjuvant. The proteins are titrated over several logs range of concentration, e.g., 1 ng to mgs., and the uric acid titrated over several logs, e.g., 10 µg to 10 mg of soluble crystalline adjuvant or 10 pg to 10 mg, and preferably 10 ng to 1 mg, of preformed crystalline adjuvant crystals. After one to several weeks, peripheral blood mononuclear cells are isolated from the patients and prepared using conventional techniques, restimulated with the appropriate antigen in vitro under standard conditions, and the development of specific cytotoxic T lymphocytes assayed in standard CTL assays. Populations at risk are immunized with the predetermined effective doses and analyzed prospectively versus controls for the incidence of disease to determine the degree of protection conferred. The amount of crystalline adjuvant administered by local inoculation will typically range from about 10 ng to about 10 mg per site, preferably about 10 µg to about 1 mg per site. For systemic administration, inoculations of crystalline adjuvant may contain about 1 mg/kg to about 1000 mg/kg of body weight.

With respect to potential toxicity of the crystalline adjuvant, local reaction to injections or other morbidity of animals immunized with any adjuvant within the scope of the invention, e.g., a crystalline adjuvant, can be readily determined. With respect to the crystalline adjuvants of the present invention displaying characteristics similar to uric acid or xanthine, significant toxicity is not expected. For example, significant levels of toxicity to uric acid or xanthine have not been observed when used in the Examples described herein. Uric acid and xanthine are normal components of mammals and local administration should be relatively safe. Uric acid is effective when injected subcutaneously, which is an effective and well tolerated immunization protocol. Uric acid and xanthine thus have favorable characteristics for an adjuvant, and crystalline molecules having similar characteristics, such as those described herein, are also expected to behave favorably as immune adjuvants.

III. Antigens

In the methods of the instant invention, the crystalline adjuvant can be used in combination with a variety of immunogens including but not limited to subunit vaccines, proteins, peptides, carbohydrates, lipids and nucleic acids (e.g., RNA and DNA), as well as whole live or attenuated organisms or altered pathogens. In certain embodiments of the invention, the antigen is a viral antigen or tumor antigen. In preferred embodiments, the antigen can be any protein antigen, especially a protein from a pathogen or tumor cell for which CTLs appear to be important to confer protective immunity. As used herein, the term pathogen means any disease-causing microorganism, including viruses, rickettsia, bacteria, and parasites, especially protozoa and helminths. A pathogen as used herein can also refer to any disease-causing molecule, including prions and abnormal host proteins, e.g. amyloid precursor protein i.e. in Alzheimer's disease.

In one embodiment, the antigen comprises at least one immunogenic protein from a pathogen, preferably from a virus or a bacterium. In another embodiment, the antigen comprises a mixture of protein or peptide epitopes derived from the antigenic proteins of a pathogenic organism. Methods of determining the epitopes of any particular protein are well known in the art (e.g., epitope mapping).

When the pathogen is a virus, the antigen can be killed or inactivated whole virus; it can be a virus-like particle comprising envelope proteins and/or glycoproteins, or it can be protein subunit or fragment thereof from a capsid or envelope antigen or an internal antigen from a virus, in which the virus is a member of families including adenovirus, picornavirus, corona virus, orthomyxovirus, paramyxovirus, herpes virus, retrovirus or papovavirus. The viral antigen can be in soluble form. In preferred embodiments, the viral antigen is in particulate form, e.g., aggregated viral antigen, or viral antigen that is bound to or encapsulated in a microsphere. Preferably, the antigen will be from a virus that causes an infection in which CTLs may play an important role in conferring immunity, such as but not limited to influenza or parainfluenza virus, retroviruses, including HIV-1, HIV-2 and SIV, PDX viruses (e.g., Varicella zoster), Herpes viruses, including Herpes simplex 1 and Herpes simplex 2, respiratory syncytial virus, rabies virus, measles virus, polio virus or rotavirus.

Inactivated, non-living whole virus preparations can be prepared in accordance with any of the techniques known to people skilled in the art, including heat inactivation, and may be used especially in preparing antigens for polio, influenza, rabies, and Japanese B encephalitis viruses. Virus-like particles are recombinantly-produced structural proteins that self assemble into structures resembling empty virions under defined conditions and are also potential candidates for vaccine development in accordance with the present invention. The preparation and characterization of recombinantly-produced virus-like particles have been described for surface proteins from several viruses, including human papilloma virus type 1 (Hagnesee et al, J. Virol., 67:315 (January 1991); human papilloma virus type 16 (Kirnbauer et al., Proc. Natl. Acad. Sci., 89:12180 (December, 1992); HIV-1 (Haffer et al., J. Virol., 64:2653 (1990), Hu et al., J. Virol., 179:321 1990); hepatitis A (Winokur, J. Virol., 65:5029 (1991); and human polyoma virus (Rose et al., in press). The teachings of the referenced articles relating to the preparation, characterization, and purification of virus-like particles are hereby incorporated by reference. These virus-like particles, which resemble live virus in external conformation but are non-infectious, may be processed and presented by class I MHC molecules of antigen presenting cells in a manner analogous to that for live virus and are good candidates for vaccine development.

For many viruses, one or more individual antigens may be predominantly important for conferring immunity, including a CTL component, so that vaccines can be comprised of that protein subunit, or immunogenic fragment thereof. One example is the surface antigen of the hepatitis B virus, HBSag, that is secreted from cells and present in the blood of infected human beings. A second example is the influenza hemagglutinin (HA) antigen, which can be chemically removed from the virus capsid or produced recombinantly using techniques that are old and well known in the art.

Protein subunits and fragments can be obtained by conventional techniques, such as proteolysis, chemical treatment, or solubilization and purification of the relevant protein from the native virus, they can be prepared using automated peptide synthesis techniques, or they can be produced by recombinant DNA techniques and then purified in accordance with procedures known to persons skilled in the art. When the antigen is obtained through recombinant DNA techniques, DNA including that encoding the antigen of interest is cloned into an expression vector, such as a vaccinia virus, baculovirus, plasmid, or phage and expressed in a suitable prokaryotic or eukaryotic expression system, in accordance with established protocols. See, Sambrook, Fitsch, & Maniatis, Molecular Cloning, Chapters 8 and 9 (second edition, 1989), which are hereby incorporated by reference.

When the antigen is from a bacterium, the antigen can be from inactivated bacteria, it can be from a toxin or a capsular polysaccharide, or it can be a subunit antigen. Preferably, the antigen is from a bacteria where cellular immunity appears to be important for providing protection against infection or reinfection, for example bacteria causing tuberculosis (*Mycobacteria tuberculosis*); leprosy (*Mycobacterium leprae*), brucellosis (*Brucella* spp.) and listeriosis (*Lysteria monocytogenes*). Such antigens can be prepared readily by persons skilled in the art, by traditional or recombinant DNA techniques.

In yet another embodiment of the invention, the antigen can be from a parasite where CTL response appears to be important for conferring immunity. Such parasites include members from the class Apicomplexa, which includes *Plasmodium* species that are the etiologic agents of infectious malaria and *Toxoplasmosis gondii*, the etiologic agent of toxoplasmosis. Also included are antigens from *Leischmania* species.

Tumor-associated antigens, i.e., antigens associated with neoplastic disease, can also be used as the antigens with uric acid in the methods of the invention. In nonlimiting embodiments, the tumor antigen can be an antigen associated with human melanoma, colonic carcinoma, breast carcinoma, or renal carcinoma. It has previously been shown, for example, that autologous CTLs recognize a total of six independent antigens on human melanoma cells, which can be used with uric acid to stimulate an immune response in methods of the invention. See, Van Der Bruggen, et al., Science, 254:1643 (December, 1991).

IV. Antigen-Presenting Cells

A. Sources of Antigen-Presenting Cells

The antigen-presenting cells, e.g., dendritic cells, mononuclear phagocytes, or B lymphocytes, used in this invention can be isolated as described herein or by methods known to those skilled in the art. In a preferred embodiment, human antigen-presenting cells are used from an appropriate tissue source, preferably blood or bone marrow.

Mature dendritic cells can be obtained by culturing proliferating or non-proliferating dendritic cell precursors in a culture medium containing factors which promote maturation of immature dendritic cells to mature dendritic cells. Steinman et al. U.S. Pat. No. 5,851,756 and U.S. application Ser. No. 08/600,483 (WO 97/29182) report methods and compositions for obtaining dendritic cells and are incorporated herein by reference.

Other antigen-presenting cells, e.g. B lymphocytes and mononuclear phagocytes, e.g, macrophages, can also be obtained using well known methods. For example, macrophages can be obtained by induction in vivo followed by harvesting the macrophages, e.g, by peritoneal exudates. Macrophages can be also obtained and purified from tissues, e.g., spleen, or grown from precursors in the bone marrow with mCSF according to methods well known in the art. Macrophage precursors, e.g. blood monocytes, can be obtained from bone marrow according to methods well known in the art.

The antigen-presenting cell precursors, e.g., dendritic cell precursors, from which the immature antigen-presenting cells, e.g., dendritic cells, for use in this invention are derived, are present in blood as PMBCs. Although most easily obtainable from blood, the precursor cells may also be obtained from any tissue in which they reside, including bone marrow and spleen tissue. When cultured in the presence of cytokines such as a combination of GM-CSF and IL-4 or IL-13 as described below, the non-proliferating precursor cells give rise to immature antigen-presenting cells, e.g., dendritic cells for use in this invention.

B. Culture of Pluripotential PMBCs to Produce Immature Dendritic Cells.

Dendritic cell development can be divided into 4 stages: 1) a proliferating progenitor that can be either dendritic cell committed or uncommitted and capable of maturing to a nondendritic cell, 2) a non-proliferating precursor like the blood monocyte that does not show dendritic cell properties but is the starting population for many clinical studies, 3) an immature dendritic cell which has properties and commitment to become a dendritic cell, e.g. specialized antigen capture mechanisms including apoptotic cells for presentation, and MHC rich compartments, and 4) finally, the mature T cell stimulatory dendritic cell.

Cultures of immature dendritic cells, i.e. antigen-capturing phagocytic dendritic cells, may be obtained by culturing the non-proliferating precursor cells in the presence of cytokines which promote their differentiation. A combination of GM-CSF and IL-4 at a concentration of each at between about 200 to about 2000 U/ml, more preferably between about 500 and 1000 U/ml, and most preferably about 800 U/ml (GM-CSF) and 1000 U/ml (IL-4) produces significant quantities of the immature, i.e. antigen-capturing phagocytic dendritic cells, dendritic cells. Other cytokines or methods known in the art which efficiently generate immature dendritic cells may be used for purposes of this invention. Examples of other cytokines which promote differentiation of precursor cells into immature dendritic cells include, but are not limited to, IL-13. Maturation of dendritic cells requires the addition to the cell environment, preferably the culture medium, of a dendritic cell maturation factor which may be selected from monocyte conditioned medium and/or factors including TNF-alpha, IL-6, IFN-alpha, and IL-1-beta.

V. Vaccines

A pharmaceutical composition of the invention comprising crystalline adjuvant (e.g., uric acid or xanthine) and antigen can be administered, preferably in sterile form, to a subject to immunize the subject against a disease. A pharmaceutical composition of the invention can thereby be used as a vaccine. Crystalline adjuvants and antigens of the invention are particularly useful in vaccinating mammalian hosts for CTL immunity. A pharmaceutical composition of the invention may be useful in the treatment of infectious diseases, e.g., HIV-1 and HIV-2, where CTL response to infection may play an important role.

The preparation of vaccines is well understood in the art. The active ingredients are often mixed with excipients which are pharmacologically acceptable and compatible with the active ingredient. Suitable excipients are, for example, water, saline, dextrose, glycerol, ethanol, or the like and combinations thereof, with saline being particularly preferred. Preferably, pharmaceutical compositions of the invention are in sterile form.

The vaccines are administered in a manner compatible with the dosage formulation, and in such amount as will be therapeutically effective and immunogenic. For example, vaccines of the invention comprising crystalline adjuvant (e.g., uric acid or xanthine) and antigen can be administered intradermally, transdermally, orally, intranasally, intramuscularly, subcutaneously, intravenously or intraperitoneally by a variety of methods known to those skilled in the art, including but not limited to needle and syringe administration, microseeding, transdermal patch, inhalation, spray, tablet, liquid drink, and biolistics. The quantity to be administered depends on the subject to be treated, capacity of the subject's immune system to generate a cellular immune response, and degree of protection desired. The crystalline adjuvant (e.g., uric acid or xanthine) can be used in combination with a variety of immunogens or antigens, which are the active ingredient of the vaccine, including but not limited to subunit vaccines, proteins, peptides, carbohydrates, lipids and nucleic acids, as well as whole live or attenuated organisms or altered pathogens. Precise amounts of antigen required to be administered depend on the judgment of the practitioner. However, suitable dosage ranges are of the order of about one microgram to about one milligram, preferably about 500 to 800 micrograms, and preferably about 1 microgram and more preferably about 5 micrograms, and more preferably 100 micrograms active ingredient per kilogram bodyweight individual.

In accordance with the present invention, the vaccine contains crystalline adjuvant (e.g., uric acid or xanthine) as an adjuvant which enhances the effectiveness of the vaccine. In one aspect of the invention, the antigens are presented to antigen presenting cells of the immune system in the presence of crystalline adjuvant (e.g., uric acid or xanthine). Thus, in one embodiment, the antigen and crystalline adjuvant (e.g., uric acid or xanthine) can be prepared as an injectable, either as liquid solutions or suspensions, and simultaneously injected into the mammal to be immunized. The antigen and crystalline adjuvant (e.g., uric acid or xanthine) either can be free in the liquid solutions or suspensions, or can be encapsulated in a depot or other controlled release vehicle.

Suitable regimes for initial administration and booster shots are variable, but are typified by an initial administration followed by a subsequent administration. In some cases, a single dose may be sufficient to induce immunity and/or alleviate symptoms in a subject. In other cases a typical prime boost regimen is implemented, with the precise number of boosts needed for any single vaccine containing the multivalent conjugates to be determined by measuring the desired immunological outcomes relevant to the specific vaccine (e.g., antibody titer, delayed type hypersensitivity response, proliferation of B and/or T cells, cytokine, cytotoxic and/or chemokine responses).

Vaccines of the instant invention can be tested for their ability to induce an immune response. Examples of methods for assaying for immune response to vaccines are readily available, e.g., Immunobiology. 5th ed., Appendix I: A36-A41, Janeway, Charles A.; Travers, Paul; Walport, Mark; Shlomchik, Mark. New York and London: Garland Publishing, c2001. For example, a suitable animal model can be used to determine whether a candidate vaccine comprising an antigen and crystalline adjuvant (e.g., uric acid or xanthine) of the invention can confer immunity against infection with a live pathogen or whole tumor cells. The ability of a given antigen and crystalline adjuvant (e.g., uric acid or xanthine) to confer protective immunity against infectious disease in a animal can be established using challenge assays, such as lethal or sub-lethal challenge assays, known in the art. For example, where the animal model is a laboratory animal such as a mouse or a rat and the antigen is a viral antigen, the animal is immunized with the candidate antigen and crystalline adjuvant (e.g., uric acid or xanthine) of the invention via a suitable route of administration, such as subcutaneously, intravenously or intraperitoneally, with or without boosting, and subsequently challenged with lethal doses of virus in a suitable carrier. Survival of the immunized animals is monitored and compared to virus-immune positive control and negative control animals, which have been immunized with live virus and with antigen in the absence of crystalline adjuvant (e.g., uric acid or xanthine), respectively. A lethal challenge assay that can be used is described, for example, in Dillon et al, Vaccine, 10:309 (1991).

The crystalline adjuvant (e.g., uric acid or xanthine) and antigen(s) of the invention can be used in CTL vaccine development. In one embodiment, the crystalline adjuvant (e.g., uric acid or xanthine) and antigen(s) as described herein are evaluated for their activity in an in vitro antigen presenting assay. The identification method involves obtaining a plurality of potentially immunogenic antigens from a pathogen, such as a virus, for which a CTL vaccine is sought; adding the antigens and crystalline adjuvant (e.g., uric acid or xanthine) to a population of antigen presenting cells, including macrophages, and lymphokine secreting CTLs or antigen-specific T-T hybridomas that previously have been stimulated with an appropriate antigen, such as a whole virus; and selecting a complex including a antigen recognized by the previously stimulated CTLs. This in vitro assay system enables the identification of active complexes and can also optimize identification of the component of the pathogen recognized by CTLs. One of several antigen presentation assays known in the art can be used in this in vitro screen. Preferred assays will employ a read out that measures lymphokine or serine esterase production by CTLs or by class I-restricted T-T hybridomas. Alternatively, if the subpopulation of macrophages that have the ability to present exogenous antigen in association with class I can be lysed by CTLs, the read out system can employ a standard chromium release assay well known to those of skill in the art. The preparation of class I restricted T-T hybridomas using a BW5147 cell line transfected to express the CD8 gene has been described in the literature (Rock et al., J. Immunol., 145:804 (1990), the teachings of which are hereby incorporated by reference. These techniques can be used to prepare antigen-specific, class I-restricted T-T hybridomas useful in the screening assays of the invention. Antigens that elicit a strong CTL response in vitro are good candidates for vaccine development for infectious diseases or tumor-associated pathological disorders where the cellular arm of the immune response may be important to confer complete protection.

VI. Pharmaceutical Compositions

Another aspect of the invention pertains to pharmaceutical compositions comprising the agents (e.g., crystalline adjuvant, e.g. uric acid or xanthine and antigen) of the invention. In one embodiment of the invention, crystalline adjuvant (e.g., uric acid or xanthine) and antigen are used in pharmaceutical compositions that, when administered to a mammalian host in an effective amount, are capable of activating antigen-presenting cells or are capable of inducing an antigen-specific response in T lymphocytes. In accordance with the present invention, pharmaceutical compositions of the invention will have utility in both medical and veterinary applications and can be used therapeutically, as well as prophylactically. The term mammal as used herein includes both human and non-human primates, including chimpanzees and monkeys, and domesticated mammals, such as dogs, cats, rabbits, guinea pigs, pigs, cows, horses, sheep, and goats, as well as common laboratory animals such as mice, rats, and hamsters. The compositions of the invention are administrated to a mammal in need of such treatment, such as a mammal at risk of infection from or infected with a pathogenic organism or bearing a tumor or at risk of developing a tumor-related disorder, in an effective amount.

The pharmaceutical compositions of the invention typically comprise a sterile crystalline adjuvant, preferably uric acid, and antigen (soluble or particulate) and a pharmaceutically acceptable carrier. The carrier must be pharmaceutically acceptable, in the sense of being compatible with the active ingredient(s) of the pharmaceutical composition and not deleterious to the recipient thereof. As used herein "pharmaceutically acceptable carrier" includes any and all solvents, dispersion media, coatings, antibacterial and antifungal agents, isotonic and absorption delaying agents, and the like that are physiologically compatible. Examples of suitable carriers are, for example, water, saline, dextrose, glycerol, ethanol or the like, and combinations thereof. Pharmaceutically acceptable carriers include sterile aqueous solutions or dispersions and sterile powders for the extemporaneous preparation of sterile injectable solutions or dispersion. According to the instant invention, preferred pharmaceutical compositions would include sterile components, e.g. sterile forms of crystalline adjuvant, antigen and pharmaceutically acceptable carrier. Methods of sterilizing the components of pharmaceutical compositions of the instant invention are commonly known in the art. The use of such media and agents for pharmaceutically active substances is well known in the art. Except insofar as any conventional media or agent is incompatible with the active compound, use thereof in the pharmaceutical compositions of the invention is contemplated. Supplementary active compounds can also be incorporated into the compositions.

The type of carrier can be selected based upon the intended route of administration. Administration of the pharmaceutical compositions of the invention may be by any suitable route including oral, nasal, mucosal, buccal, rectal, topical and parenteral, with oral and parenteral routes, including subcutaneous, intramuscular, intravenous, and intradermal. Accordingly, in various embodiments, the carrier is suitable for, intravenous, intraperitoneal, subcutaneous, intramuscular, transdermal or oral administration. In a preferred embodiment, the composition is formulated such that it is suitable for subcutaneous administration.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as manitol, sorbitol, or sodium chloride in the composition. Prolonged absorption of the injectable compositions can be brought about by including in the composition an agent which delays absorption, for example, monostearate salts and gelatin. Moreover, the compositions can be administered in a time release formulation, for example in a composition which includes a slow release polymer. The active compounds can be prepared with carriers that will protect the compound against rapid release, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, polylactic acid and polylactic, polyglycolic copolymers (PLG). Many methods for the preparation of such formulations are patented or generally known to those skilled in the art.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Depending on the route of administration, the agent may be coated in a material to protect it from the action of enzymes, acids and other natural conditions which may inactivate the agent. For example, the agent can be administered to a subject in an appropriate carrier or diluent co-administered with enzyme inhibitors or in an appropriate carrier such as liposomes. Pharmaceutically acceptable diluents include saline and aqueous buffer solutions. Enzyme inhibitors include pancreatic trypsin inhibitor, diisopropylfluorophosphate (DEP) and trasylol. Liposomes include water-in-oil-in-water emulsions as well as conventional liposomes (Strejan, et al., (1984) *J. Neuroimmunol* 7:27). Dispersions can also be prepared in glycerol, liquid polyethylene glycols, and mixtures thereof and in oils. Under ordinary conditions of storage and use, these preparations may contain a preservative to prevent the growth of microorganisms.

The active agents in the composition (i.e., uric acid or xanthine and antigen) preferably are formulated in the composition in a therapeutically effective amount. A "therapeutically effective amount" refers to an amount effective, at dosages and for periods of time necessary, to achieve the desired therapeutic result, such as the activation of antigen-presenting cells or the induction of an antigen-specific T lymphocyte response, to thereby influence the therapeutic course of a particular disease state. A therapeutically effective amount of an active agent may vary according to factors such as the disease state, age, sex, and weight of the individual, and the ability of the agent to elicit a desired response in the individual. Dosage regimens may be adjusted to provide the optimum therapeutic response. A therapeutically effective amount is also one in which any toxic or detrimental effects of the agent are outweighed by the therapeutically beneficial effects. In another embodiment, the active agent is formulated in the composition in a prophylactically effective amount. A "prophylactically effective amount" refers to an amount effective, at dosages and for periods of time necessary, to achieve the desired prophylactic result, for example, influencing the induction of an antigen-specific T lymphocyte response sufficient for prophylactic purposes. Typically, since a prophylactic dose is used in subjects prior to or at an earlier stage of disease, the prophylactically effective amount will be less than the therapeutically effective amount.

A non-limiting range for a therapeutically or prophylactically effective amount of the crystalline adjuvant, e.g., uric acid or xanthine, and antigen is about 10 ng to about 100 g and about 10 pg to about 100 mg, respectively. It is to be noted that dosage values may vary with the severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

The amount of active compound in the composition may vary according to factors such as the disease state, age, sex, and weight of the individual. Dosage regimens may be adjusted to provide the optimum therapeutic response. For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

An agent (e.g. uric acid or xanthine and antigen) of the invention can be formulated into a pharmaceutical composition wherein the agent is the only active compound therein. Alternatively, the pharmaceutical composition can contain additional active compounds. For example, two or more agents may be used in combination. Moreover, an agent of the invention can be combined with one or more other agents that have immunomodulatory properties. For example, uric acid and antigen may be combined with one or more cytokines or with other known immune adjuvants.

In certain embodiments, a pharmaceutical composition of the invention can be packaged with instructions for using the pharmaceutical composition for a particular purpose, such as to modulate an immune response, for use as an adjuvant, to modulate an allergic response or to modulate an autoimmune disease.

VII. Inflammations and Autoimmune Diseases

As demonstrated by the Examples provided herein, the induction of cell injury leading to apoptosis causes an increase in cellular production of uric acid. As described herein, the amount of uric acid providing a strong adjuvant effect can be produced by about $2\times10^6$ injured mammalian cells, a level of cell death that would reasonably occur in situations of inflammation. It is known that uric acid can be produced in large amounts in vivo as a result of tissue injury. Necrosis of cells is also known to result in the release of uric acid. An increased local concentration of uric acid occurring secondary to tissue injury may contribute to the inflammation associated with tissue injury. Consistent with these findings, applicants have demonstrated that reduction of uric acid by administration of uricase reduces inflammation in response to dying cells in a mouse model.

Accordingly, in one aspect of the invention, therapeutic methods are provided for preventing or treating inflammations, e.g., inflammations associated tissue injury, in a subject by using an agent that reduces uric acid concentration. Preferably, the subject to be treated for inflammation does not exhibit systemic hyperuricemia, e.g., hyperuricemia associated with abnormally high serum levels of uric acid, but displays increased amounts of uric acid locally, e.g., at sites of inflammation. Preferably, the subject to be treated for inflammation has normal serum levels of uric acid, e.g., uric acid serum levels ranging from about 15-80 µg/ml, preferably from about 20-70 µg/ml, more preferably from about 30-65 µg/ml and even more preferably from about 40-60 µg/ml. The subject may have an increased concentration of uric acid in serum due to a local or systemic inflammation, e.g., concentrations greater than about 30 µg/ml, 40 µg/ml, 50 µg/ml, 60 µg/ml, 70 µg/ml, 80 µg/ml or 90 µg/ml. The preferred subject to be treated has normal serum levels of uric acid and a local increased concentrations of uric acid at sites of inflammation, e.g., due to the presence of injured, dying or dead cells. Local concentrations of uric acid can be greater than about 40 µg/ml, 50 µg/ml, preferably greater than about 60 µg/ml, and more preferably greater than about 70 µg/ml, 80 µg/ml or 90 µg/ml. In preferred embodiments, the subject has local formation of MSU crystals at sites of inflammation, e.g., MSU crystal formation at sites of inflammation due to increased local concentrations of uric acid to concentrations at which uric acid crystallizes in vivo.

Inflammations to be treated with uric acid reducing agents include acute inflammations and chronic inflammations. Acute inflammation is associated with disorders in which tissue inflammation is generally of relatively short duration, and lasts from about a few minutes to about one to two days, although it may last several weeks. The main characteristics of acute inflammatory disorders include increased blood flow, exudation of fluid and plasma proteins (edema) and emigration of leukocytes, such as neutrophils. Acute inflammatory disorders are also characterized by heat, redness, swelling, pain and loss of function. Examples of acute inflammations for which treatment with uric acid reducing agents are useful include, but are not limited to inflammations associated with myocardial infarction, strokes or other ischemic injury, inflammations post trauma or post surgery, inflammations from toxic agents or from the injury of cells that occurs during innate or adaptive immune responses. Chronic inflammatory disorders are generally of longer duration, e.g., weeks to months to years or even longer, and are associated histologically with the presence of lymphocytes and macrophages and with proliferation of blood vessels and connective tissue and ongoing tissue damage. Chronic inflammatory disorders are generally characterized by heat, redness, swelling, pain and loss of function. Examples of causes of chronic inflammatory disorders that can be treated according to the methods of the invention include, but are not limited to, microbial infections (e.g., bacterial, viral and fungal infections), physical agents (e.g., burns, radiation, and trauma), chemical agents (e.g., toxins and caustic substances), chronic or repeated injury (e.g., osteoarthritis), tissue necrosis and various types of immunologic reactions. Examples of chronic inflammatory disorders, include, but are not limited to osteoarthritis, rheumatoid arthritis, asthma, cystic fibrosis, chronic infections (e.g., to Schistosomiasis, Papilloma, *Helicobacter*, Hepatitis B and C, EBV, HPV); inflammatory bowel disease (IBD), Crohn's disease, psoriasis, atopic eczema, acne, systemic lupus erythematosis, multiple sclerosis, atherosclerosis, restenosis; chronic bronchitis, sinusitis, chronic gastroenteritis and colitis; chronic cystitis and urethritis; hepatitis; chronic dermatitis; chronic conjunctivitis; chronic serositis (pericarditis, peritonitis, synovitis, pleuritis and tendinitis); uremic pericarditis; chronic cholecystis; chronic vaginitis; and chronic uveitis.

Uric acid concentrations in a subject can be reduced with uric acid reducing agents either systemically or locally, e.g, in the vicinity of the acute inflammation. Such uric acid reducing agents can be administered to existing acute inflammations, or may be administered prophylactically to individuals at risk of developing acute inflammations. Agents useful for reducing concentrations of uric acid associated with inflammation in a subject include, but are not limited to, agents that increase excretion of uric acid, e.g. uricosuric agents, agents that inhibit uric acid synthesis, and agents capable of degrading uric acid. Methods provided herein can be used to identify an agent useful for reducing inflammation associated with cell injury. In one embodiment, a method useful for identifying an agent useful for cell injury involves contacting an apoptotic cell with a test agent and assaying for an indicator of uric acid production, whereby an agent is identified based on its ability to reduce uric acid produced by said apoptotic cell in comparison to a suitable control. A "suitable control" is any control or standard familiar to one of ordinary skill in the art useful for comparison purposes. For example, suitable controls can be an appropriate solvent or dispersion medium, e.g., containing, for example, water, ethanol, polyol (e.g., glycerol, propylene glycol and liquid polyethylene glycol and the like) and suitable mixtures thereof used for dilution and/or delivery of the potential uric acid reducing agent to the cells or subject. Suitable controls can be, for example, cell culture medium, PBS, saline and the like. Examples of agents useful for reducing uric acid concentration in a subject include, but are not limited to: uricase, allopurinol, probenicid, sulfinpyrazone, benzbromarone, zoxazolamine, diflunisal, aspirin and tienilic acid, E5050, FK366, CGS12970, Ambroxol and AA193 [5 chloro-7,8-Dihydro-3-phenyl furol (2,3G)-1,2-bensizoxazole]. In preferred embodiments, agents capable of degrading uric acid, such as uricase (urate oxidase), are used to reduce local uric acid concentrations in a subject. Anti-MSU crystal antibodies are also envisioned by the instant inventors as useful for reducing uric acid concentrations in a subject. Antibodies that recognize crystals are known to those skilled in the art, e.g., see Kam M., Perl-Treves D., Sfez R., Addadi L. (1994) "Specificity in the recognition of crystals by antibodies" *Journal of Molecular Recognition* 7(4):257-64. In other embodiments, agents capable of inhibiting inflammation are any agents that would modulate, e.g., downmodulate, e.g., inhibit the ability of urate crystals to bind to cells, such as T cells. In one embodiment, an agent capable of inhibiting inflammation is an agent that downmodulates, e.g., inhibits, the ability of urate crystals to bind and activate cells, e.g., T cells. Agents useful for blocking the ability of urate crystals to bind to and/or activate cytotoxic T cells include agents that would downmodulate the binding of MSU crystals to a receptor (e.g., a receptor to which MSU crystals bind) on the cells, e.g., a receptor involved in signaling activation of the cells.

It will be understood that the instant invention further envisions that other endogenous crystalline adjuvants including, but not limited to, xanthine or hypoxanthine, may contribute to inflammation, e.g., inflammation due to injured, dying or dead cells. Accordingly, also within the scope of the instant invention are therapeutic methods involving agents that reduce the concentration of other endogenous crystalline adjuvants, e.g., xanthine or hypoxanthine crystals, to prevent or treat inflammation, e.g., inflammation due to injured, dying or dead cells. Such agents are known or can be identified according to standard methods known to those of ordinary skill in the art.

In another aspect of the instant invention, therapeutic methods are provided for treating autoimmune diseases. Many autoimmune disorders are the result of inappropriate activation of T cells that are reactive against self tissue and that promote the production of cytokines and autoantibodies involved in the pathology of the diseases. It is likely that increased local concentrations of uric acid contribute to the genesis, persistence and/or pathology of such auto-immune diseases. It has been shown that modulation of T helper-type responses can either have a beneficial or detrimental effect on an autoimmune disease. Other autoimmune diseases may be ameliorated by a Th1-type response. Auto-immune diseases may potentially be treated using an agent that reduced the concentration, preferably local concentration, of uric acid, as provided in the instant invention. The treatment may be further enhanced by administrating a Th1-promoting cytokine (e.g., IFN-γ) to the subject in amounts sufficient to further stimulate a Th1-type response. Examples of agents that can be used to reduce the concentration of uric acid in a subject include, but are not limited to, agents that increase excretion of uric acid, e.g. uricosuric agents, agents that inhibit uric acid synthesis, and agents capable of degrading uric acid. Examples of agents useful for reducing uric acid concentration in a subject include, but are not limited to: uricase, allopurinol, probenicid, sulfinpyrazone, benzbromarone, zoxazolamine, diflunisal, aspirin and tienilic acid, E5050, FK366, CGS12970, Ambroxol and AA193 [5 chloro-7,8-Dihydro-3-phenyl furol (2,3G)-1,2-bensizoxazole].

Depending on the disease, the reducing agent may be administered either systemically or locally. For example, in the case of rheumatoid arthritis, the agent may be administered directly into the joints. For systemic treatment, the reducing agent preferably is administered intravenously.

The efficacy of agents for treating autoimmune diseases can be tested in the above described animal models of human diseases (e.g., EAE as a model of multiple sclerosis and the NOD mice as a model for diabetes) or other well characterized animal models of human autoimmune diseases. Such animal models include, but are not limited to, the mrl/lpr/lpr mouse as a model for lupus erythematosus, murine collagen-induced arthritis as a model for rheumatoid arthritis, and murine experimental myasthenia gravis (see Paul ed., *Fundamental Immunology*, Raven Press, New York, 1989, pp. 840-856). An agent that reduced the concentration or uric acid, preferably the local concentration of uric acid, e.g. uricase, is administered to test animals and the course of the disease in the test animals is then monitored by the standard methods for the particular model being used. Effectiveness of the reducing agent is evidenced by amelioration of the disease condition in animals treated with the agent as compared to untreated animals (or animals treated with a control agent). In the case where a systemic agent is used to reduce the concentration of uric acid, the effectiveness of the reducing agent can also be monitored by measuring a reduction in uric acid levels in serum.

Non-limiting examples of autoimmune diseases and disorders having an autoimmune component that may be treated according to the invention include: diabetes mellitus, inflammatory bowel disease, arthritis (including rheumatoid arthritis, juvenile rheumatoid arthritis, psoriatic arthritis), multiple sclerosis, myasthenia gravis, systemic lupus erythematosis, autoimmune thyroiditis, dermatitis (including atopic dermatitis and eczematous dermatitis), psoriasis, Sjögren's Syndrome, including keratoconjunctivitis sicca secondary to Sjögren's Syndrome, alopecia areata, allergic responses due to arthropod bite reactions, Crohn's disease, aphthous ulcer, iritis, conjunctivitis, keratoconjunctivitis, ulcerative colitis, asthma, allergic asthma, cutaneous lupus erythematosus, scleroderma, vaginitis, proctitis, drug eruptions,leprosy reversal reactions, erythema nodo sum leprosum, autoimmune uveitis, allergic encephalomyelitis, acute necrotizing hemorrhagic encephalopathy, idiopathic bilateral progressive sensorineural hearing loss, aplastic anemia, pure red cell anemia, idiopathic thrombocytopenia, polychondritis, Wegener's granulomatosis, chronic active hepatitis, Stevens-Johnson syndrome, idiopathic sprue, lichen planus, Graves ophthalmopathy, sarcoidosis, primary biliary cirrhosis, uveitis posterior, and interstitial lung fibrosis.

The invention is further illustrated by the following examples, which should not be construed as further limiting. The contents of all references, pending patent applications and published patents, cited throughout this application are hereby expressly incorporated by reference.

EXAMPLES

Materials and Methods Used in Examples I-VII

Mice, Cells and Reagents

Mice were obtained from Jackson laboratories (Bar Harbor, ME). All biochemical reagents were purchased from Sigma, (St. Louis, MO). Uric acid detection kits were purchased from Molecular Probes (Eugene, OR). MSU crystals were prepared from a supersaturated uric acid solution (>300 µg/ml) in pH 8.5 0.1 M borate, washed twice with absolute alcohol and once with acetone, and were then air dried. All other mice, cells and reagents were as previously described.[15,16] HIV-gp120 and ovalbumin microspheres were prepared as previously described.[16] HIV gp120 peptide RGPGRAFVTL (SEQ ID NO: 1) and ovalbumin peptide SIINFEKL(SEQ ID NO: 2) were produced by Corixa (Seattle, WA).

Purification and Treatment of LMW Adjuvant

To obtain primary liver cells, livers were dissected from mice, sliced and then ground into a single-cell suspension. Cell cytosol from UV-treated 3T3 cells or primary liver cells was produced by nitrogen cavitation, dounce homogenization and differential centrifugation as previously described.[16] Chromatographic separations were performed with a Beckman System Gold 125 solvent module linked to a System Gold 168 diode array spectrum analyzer running Gold Nouveau software (ver 1.0). Cytosolic fractions were purified sequentially on Zobrax GF-250 (Agilent) or Superdex 75 HR 10/30 (Pharmacia), Mono Q HR 5/5 (Pharmacia), Superdex 200 HR 10/30 (Pharmacia) and semi-preparative C18 (Vydac) columns. HPLC running conditions and buffers are described below. For determining susceptibility to uricase, one fortieth of a liver-equivalent of LMW C18 fraction was incubated at room temperature in 500 µl of 0.1 M pH 8.5 borate buffer for 4 minutes, and then 0.01 unit uricase was added and the UV absorption at 292 nm was measured. In adjuvant experiments in vivo, one tenth of a liver-equivalent of LMW C18 fraction was treated with 0.1 unit uricase at room temperature before injection in vivo.

Immunization and CTL Assays

Immunization of mice with antigen-polystyrene beads (2-10 µg) +/− cytosolic fractions and assays for the priming of CTL were performed as previously described [16]. Fractions from the GF-250 column were injected without further manipulation, while fractions from all other columns were dried and reconstituted to normal osmolarity before injection. Fractions from 1%-10% of liver cytosol were typically injected into mice. Pooled fractions without adjuvant activity were standardly used as negative controls. For in vitro stimulation, splenocytes from immunized mice were stimulated directly with $10^{-8}$ M peptide (RGPGRAFVTL-SEQ ID NO: 1 or SIINFEKL-SEQ ID NO: 2) and were then assayed as previously described.[16]

Mass Spectrometry

Trimethylsilyl (TMS) derivatives were formed by addition of 25 µl of silylating reagent (N,O-bis-(trimethylsilyl)trifluoroacetamide, pyridine, hexamethyldisilazane and trimethylchlorosilane; 13:2:1:10 v:v) and heating at 100° C. for 30 minutes. Next, 2 µl of this solution was analyzed by GC-MS using a Waters Quattro-II triple quadrupole GC-MS system with a J & W Scientific DB-23 fused silica capillary column (0.25 mm×30 m, 0.25 µm phase thickness) in the splitless injection mode with He as the carrier gas at 0.9 ml/min. The column temperature was programmed from 100° C. to 255° C. at 10° C/min. Injector and transfer lines were maintained at 225° C. Positive ion electron impact ionization was used with the source temperature at 200° C. and the ionization energy at 70 eV. Full mass spectra were acquired from m/z 40 to 800 at 1 sec. intervals. For ESI MS, the equivalent of one-twentieth of a liver, or $4 \times 10^7$ UV-treated 3T3 cells, of the active fraction from the C18 column was suspended in 50/50 methanol: water in preparation for the injection. Negative ion electrospray mass spectra were acquired by direct infusion at 3 µl/min using a Finnigan LCQ quadrupole ion trap mass spectrometry system with the electrospray voltage at 4 kV and the capillary at 175 V. MS2 and MS3 product ion spectrum of m/z 167 and 124 were acquired with normalized collision energies of 42% and 30%, respectively.

Uric Acid Measurement in Treated Cells

EL4 cells ($10^8$) were resuspended in 5 ml of culture media and incubated at 37° C. for 5 hours after being treated for one hour with emetine[16] or cycloheximide or heat shocked for 20 minutes at 45° C. (see FIG. 3J). 3T3 cells grown in 15 cm dishes were either untreated or exposed to UV light for 5 minutes and incubated in 5 hours. The cells were suspended without washing and disrupted by nitrogen cavitation followed by centrifugation, as described.[16] The resulting supernatants were diluted with 0.1 M borate, and analyzed for uric acid content using a uric acid detection kit (Molecular Probes).

Dendritic Cell Culture and Analysis

Bone marrow was cultured for 7 days in media containing 10 u/ml of both GM-CSF and IL-4, as previously described.[24] Fresh media (50% volume) containing cytokines was added at the 4th day of culture. At day 7, floating cells were removed by aspiration after gentle rocking, and soluble or crystalline uric acid was added. Following a 6 hour incubation, the media was gently removed and replaced with PBS containing either 0.5% heparin (sigma) or 0.5 µM polyvinyl sulfate (100 KD, Sigma) in order to detach bound crystals. Following a 10 minute incubation, cells were gently removed by scraping, washed once in 50 ml of media and 3 times with 50 ml of PBS in order to dissolve any remaining crystals, and then stained and assayed by flow cytometry as previously described.[15] To quantify MSU crystal formation in culture, a parallel set of wells was prepared without dendritic cells, and the crystals harvested by centrifugation, washed with absolute alcohol and dissolved in 0.1N NaOH. The amount of uric acid in the solubilized precipitates was determined by measuring UV absorption at 292 nM against a set of standard uric acid/NaOH solutions.

HPLC

Flow rates and protocols for different HPLC columns used in the Examples set forth below were as follows: Zobrax GP250: 120 mM NaCl and 20 mM phosphate at pH 7, 1 ml/min, isocratic elution; Mono Q: 10 mM monoethanolamine at pH 9.65 (buffer A) and 10 mM monoethanolamine with 1.5 M NaCl (buffer B) at pH 9.65, 0.5 ml/min, 0-5 min, 100% buffer A, 5-25 min, 100% buffer B; Superdex 200, 120 µM NaCl at pH 7 or water, 0.5 ml/min, isocratic elution; C18: unbuffered water (buffer A) and 80:20 acetonitrile:water (buffer B), 1 ml/min, 0-5 min, 100% buffer A, 5-20, 0-60% buffer B. For large liver cell preparations, Superdex 75 HR 10/30 column (Pharmacia) was used in place of GF-250 with identical conditions except for a flow rate of 0.5 ml/min (supplemental graph). The cytosol and cytosol fractions were lyophilized and suspended in smaller volumes of water, filtered through 0.45 and 0.2 µm membranes before injection into the HPLC or animals, except where noted. All reagents were at HPLC grade.

Example I

Identification of Endogenous Adjuvants in Cytosol from Balb/c 3T3 Cells and Balb/c Livers Cytosol from Balb/c 3T3 cells treated with UV (which have previously been shown to contain adjuvant activity)[16] or from Balb/c livers was fractionated by HPLC on a sizing column monitored with a diode array UV spectrum detector (FIG. 1A). Each four consecutive fractions (4 minutes) were pooled and tested for their ability to augment the priming of CD8 T cell responses when co-injected with particulate HIV gp120 antigen. After 14 days, splenocytes were harvested from the primed animals and were stimulated ex vivo with either antigen-transfected or peptide-pulsed syngeneic cells. The re-stimulated cells were then assayed for their ability to kill antigen-bearing target cells in a standard $^{51}$Cr-release assay.[16]

As depicted in FIG. 1B, a pool of low molecular weight (LMW) fractions that were below the optimal resolution range (<5 Kda) of the gel filtration columns possessed an adjuvant activity that markedly enhanced the generation of cytotoxic T cell responses. This pool was associated with distinct UV peaks at 235 and 292 nm (FIG. 1A). Individual components of this active LMW pool were next tested, and the majority of the activity was found to be located in a single fraction (FIG. 1B insert). This activity passed through a filter with a 3 kDa cut off. A second, distinct pool of higher molecular weight fractions (approximately 40-100 KDas) also possessed adjuvant activity.

To identify the molecular identity of the LMW adjuvant, the LMW fraction was further characterized. The adjuvant activity present in the cytosol of UV-treated 3T3 cells and the cytosol of liver cells was further purified by HLPC sequentially on anion exchange (Mono Q HR5/5) (FIG. 1C), sizing (Superdex 200 HR 10/30) (FIG. 1D) and reverse phase (C18) columns (FIG. 1E). After each separation the active fractions were identified by their ability to boost CTL responses when injected in vivo with antigen (FIGS. 1F, 1G and 1H). The active fractions from all four columns retained the unique UV absorption pattern, with peak absorptions at 235 and 292 nm (FIGS. 1C, 1D and 1E), and this pattern disappeared at low pH. The LMW adjuvant from liver chromatographed identically with that from 3T3 cells on the first HPLC column (FIG. 1I) and on all three subsequent columns, indicating that the same biologically active molecule was present in these different cell types.

At this step, the LMW material from the fourth HPLC column (C18) appeared to be homogeneous. It was collected, derivatized by trimethylsilylation (TMS) and analyzed by gas chromatography-electron impact (EI) mass spectrometry (GC-EIMS) (FIG. 2A). A single prominent GC peak was detected at 9.88 minute (FIG. 2A). The EI spectrum of this peak indicated a MW 456 compound that contained two or more TMS groups (FIG. 2B, upper panel). A search of the NIST (National Institute of Standards and Technology) database of EI mass spectra returned a very high probability match with tetra-TMS uric acid (FIG. 2B, lower panel). This same fraction was then analyzed by direct infusion negative ion electrospray ionization (ESI) tandem mass spectrometry, yielding an intense m/z 167 ion, which is consistent with it being the $[M-H]^-$ ion from uric acid. Isolation and subsequent collisional fragmentation of this ion produced an $MS^2$ product ion spectra identical to that obtained from standard uric acid. Similarly, $MS^3$ product ion spectra from the major $MS^2$ ion (m/z 124) matched that from uric acid (FIGS. 2C, 2D, 2E). The pH-dependent UV absorption peaks of the LMW adjuvant at 235 and 292 nm matched well the expected pattern for the enol tautomer of uric acid (FIG. 2F). To exclude the possibility of an enantiomeric or stereo-isomeric structure, the purified LMW molecule was incubated with uricase, a highly specific enzyme that breaks down uric acid to allantoin. Importantly, uricase rapidly destroyed the LMW molecule (FIG. 2G), identical to its effect on a uric acid standard. Together these data demonstrate that the major constituent of the highly purified LMW fraction is uric acid.

Example II

Highly Purified Uric Acid Provides Adjuvant Activity

The discovery that uric acid was the major detectable component in the highly purified LMW fraction and that this preparation had adjuvant activity in vivo, argued strongly that uric acid was responsible for the biological activity. To further evaluate this point, highly purified uric acid was tested for adjuvant activity. Highly purified uric acid (50 µg), highly purified LMW fraction from a C18 column, or PBS as control were mixed with 5 µg gp120/latex beads in 100 µl of saline and injected into two Balb/c mice. CTL from these mice were assayed for killing of 15.12 (gp120-transfected 3T3) cells (filled triangles), or vector-transfected control 3T3 cells (open squares). Results from individual mice are presented (FIG. 3A-C, wherein % Lysis indicates the degree of cell killing and the E:T ratio indicates the ratio of Effector cell: Target cell, e.g., the ratio of cytotoxic T-cell: antigen positive target cell). When injected into Balb/c mice with particulate HIV gp120, pure uric acid enhanced CTL priming to a similar degree as the purified LMW fraction (FIGS. 3A-C).

In order to demonstrate that uric acid was the active component in the LMW fraction, a similar experiment was carried out as in FIG. 3A-C in which control-treated and uricase-treated LMW fractions were used in place of uric acid and untreated LMW fractions, respectively. Importantly, treatment of the LMW fraction with uricase significantly reduced its adjuvant activity, providing further proof that uric acid was the active component in this fraction (FIG. 3D-F).

Example III

Adjuvant Activity Associated with LMW Fraction is not due to Contaminating Lipopolysaccharide Lipopolysaccharide (LPS) has potent immunostimulatory activity and is a frequent contaminant of buffers and other reagents. Although every attempt was made to avoid contamination of preparations with endotoxin, it was important to exclude the possibility that LPS was present in the LMW fraction and responsible for the adjuvant activity. Accordingly, similar experiments to those of Example II were carried out except that purified LMW fraction or commercially-obtained highly purified uric acid was injected together with antigen into toll-like receptor 4 (TLR4) null mice, which are nonresponsive to LPS. Specifically, congenic C.C3H lps-d (TLR4-/-) mice were used in place of Balb/c (TLR4+/+) mice.

As shown in FIG. 3G-I, both the purified LMW fraction and the commercial uric acid had adjuvant activity in these LPS-nonresponsive mice. These results indicated that LPS was not responsible for the adjuvant activity in the LMW fractions. These data demonstrated that commercially obtained uric acid and uric acid purified to homogeneity from liver possessed adjuvant activity. These data further showed that uricase destroyed this activity. Together, these data demonstrated that uric acid was one of the endogenous adjuvants in cells.

Example IV

Cell Stress Causes an Increase in Intracellular Levels of Uric Acid

In a previous study, it was found that the amount of endogenous adjuvant activity markedly increased in cells when they were injured by means that caused them to undergo apoptosis (e.g. treatment with UV-radiation, emetine or Fas-ligand).[16] This study further demonstrated that the increase in adjuvant activity did not require de novo protein synthesis, since it also occurred when protein synthesis was completely inhibited.[16] The present study was therefore conducted to investigate whether cell injury leading to apoptosis also causes an increase in cellular production of uric acid.

EL4 cells were either heat shocked for 20 minutes at 45° C., incubated with 25 µg/ml cycloheximide, incubated with 8 µM emetine or untreated as control. 3T3 cells were either UV-irradiated or untreated as control. These treatments were previously shown by the instant inventors to increase adjuvant activity. The amount of uric acid in the cytosol of the treated cells was determined after 5 hours of incubation. As shown in FIG. 3J, uric acid, which was below the limit of detection of our assay in untreated EL4 cells, increased dramatically following treatment of EL4 cells with heat shock, cycloheximide and emetine. An approximately 4-fold increase in uric acid was also observed when 3T3 cells were treated with UV (FIG. 3J). These results establish a correlation between cell injury and increased intracellular uric acid concentrations.

The data presented herein provide insight into the underlying mechanism for the increase in endogenous adjuvant in injured cells. Uric acid is produced during the catabolism of purines and is the end product of purine catabolism in uricotelic mammals. While not wishing to be bound by theory, the data indicate that when injured cells rapidly degrade endogenous RNA, followed by the cleavage and degradation of chromosomal DNA, purines are converted into uric acid, thereby leading to the accumulation of uric acid. Since the uric acid is not a protein and does not require protein synthesis, at least in the short term, its production is not blocked by inhibitors of protein synthesis.

In the experiments described in Examples II and III, animals were typically injected with 10-50 µg of uric acid (in 100 µl), an amount of uric acid that provided a strong adjuvant effect. To determine more precisely the amount of uric acid necessary to provide an adjuvant effect in vivo, the amount of uric acid injected into mice was titrated from 2.5-40 µg (in 100 µl; from a concentration of 25-400 µg/ml) and adjuvant activity assayed as described in Example II above. The amount of uric acid providing an adjuvant effect when injected in vivo was found to be about 10 µg (in 100 µl, or a concentration of 100 µg/ml) (FIG. 3K). This amount of uric acid is produced by about $2 \times 10^6$ UV-treated 3T3 cells (See FIG. 3J).

Example V

MSU Crystals Rapidly Activate Dendritic Cells

The activation of T cells requires secondary signals provided by molecules on APCs, called costimulators, in addition to the primary signals induced by antigen. In the absence of costimulation, T cells that encounter antigens either fail to respond and die by apoptosis or enter a state of unresponsiveness. The most well-defined costimulators for T lymphocytes are a pair of related proteins, called CD80 (B7-1) and CD86 (B7-2), that are expressed on activated professional APCs. These costimulators on APCs are recognized by specific receptors on T cells. It has been suggested that adjuvants in general, and endogenous adjuvants in particular, function at least in part by stimulating "resting" dendritic cells to mature and increase their expression of costimulatory molecules.[7,14]

Accordingly, the effect of uric acid on expression of costimulators on cultured dendritic cells was tested. Uric acid was added to cultures of primary bone-marrow derived dendritic cells. Specifically, bone marrow-derived dendritic cells from Balb/c mice in 6 well plates were untreated (thin continuous line) or incubated with 20 µl of pre-formed MSU crystals (about 1.2 mg/ml final concentration) for 6 hours (heavy dashed lines) or 24 hours (heavy continuous lines). The expression of CD80 and CD86 on CD11c+ cells was then analyzed by flow cytometry. Antibody-mediated staining of untreated cells was not significantly higher than that of background where no antibody was employed. As shown in FIG. 4A, uric acid stimulated the dendritic cells to increase their expression of CD86 and, to a slightly lesser extent, CD80, markedly and rapidly, within six hours of uric acid addition.

Next, dendritic cells from C57BL/6 (TLR4+/+) or C.C3H lps-d (TLR4−/−) mice were untreated (thin continuous lines) or incubated for 6 hours with either uric acid (70 µg/ml, a concentration at which crystals do not precipitate within 6 hours, thin dashed lines), 1 µg/ml LPS (heavy dashed lines), or 20 µl pre-formed MSU crystals (about 1.2 mg/ml final concentration) (heavy continuous lines). As depicted in FIG. 4B, the stimulatory effect induced by MSU crystals was stronger than that induced by high concentrations of LPS. As discussed in Example III, LPS has a stimulatory activity and is frequently a contaminant of reagents. Dendritic cells from the TLR4-null mice were examined to verify that LPS was not the source of the observed stimulatory activity. Importantly, the stimulatory effect was also found with cells from the TLR4-null mice, indicating the effect was not an artifact due to contaminating LPS in the uric acid preparation (FIG. 4B).

Example VI

Determination of Uric Acid Concentration Required for Adjuvant Activity

During examination of the dendritic cell cultures by microscopy, it was noted that the concentrations of uric acid that were stimulatory were also those in which crystals of uric acid precipitated. It was noted that these crystals were avidly bound by the dendritic cells. It was also observed, as depicted in FIG. 4B, that preformed crystals were highly stimulatory to dendritic cells in vitro while soluble uric acid was not. In order to determine if crystals of monosodium urate (MSU) were in fact the biologically active form in vitro, the amount of uric acid added to the cell culture was titrated and the activation of dendritic cells and crystal formation were quantified in parallel. In this experiment, dendritic cells were found to be stimulated at precisely the concentrations of uric acid that led to crystal formation (FIG. 4C). Assays with C.C3H lps-d and C57BL/6 dendritic cells yielded near identical results. This correlation indicates that MSU crystals represent the biologically active form in vitro. It is noteworthy that uric acid is reported to precipitate in vivo at the concentrations at which were injected into animals in the Examples herein (e.g. >70 µg/ml).[18] Moreover, preformed MSU crystals were found to be active when injected in vivo. These observations are consistent with MSU crystals also being the biologically active form in vivo. Data from the Examples provided herein thus indicate that a chemical phase transition is the key event that transforms a normal autologous component into a danger signal.

Example VII

MSU Crystals Play a Key Role in Inflammatory Response to Injured Cells

Figure 5:
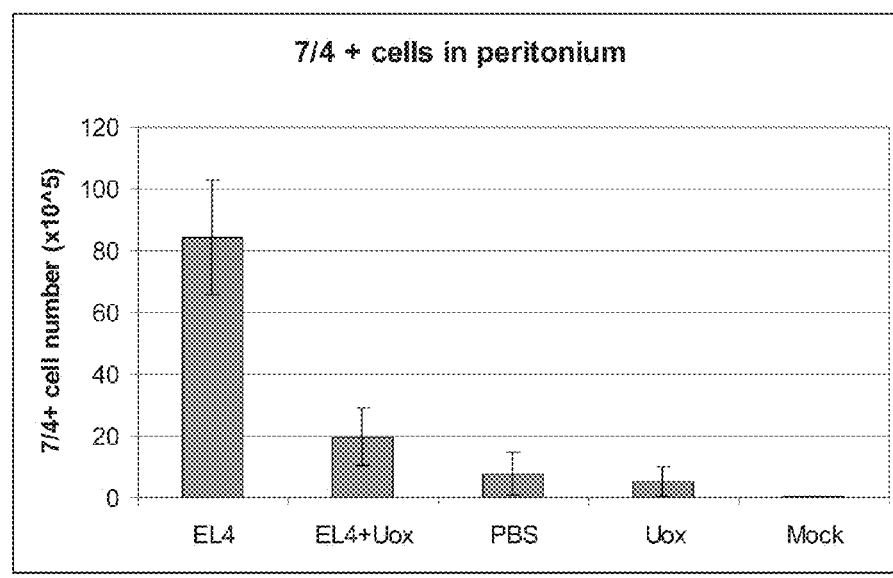
FIG. 5 is a graph depicting neutrophil infiltration following coinjection of dying EL4 cells and uricase into mice, and demonstrating that uric acid plays a key role in the inflammatory response to dying cells. Animals normally mount an inflammatory response to the injection of dead or dying cells, and subsequent neutrophil infiltration into the peritoneum is an indicator of the resulting inflammatory response. Dying EL4 cells were prepared by exposing EL4 cells to heat shock treatment for 10 minutes followed by incubation at 37° C. for 7 hours. C57BL/6 mice were then injected peritoneally with either dying EL4 cells alone, dying EL4 cells coinjected with 10 μg uricase, PBS alone, uricase alone, or were untreated as controls. Peritoneal fluid was harvested 17 hours after injection and the amount of neutrophils present was measured by flow cytometry using an antibody (7/4 Ab) that specifically stains neutrophils

The role of MSU crystals in the inflammatory response to dying cells was next examined in vivo. It is known that animals normally mount an inflammatory response in response to the injection of dead or dying cells. Following injection with dead or dying cells, subsequent neutrophil infiltration into the peritoneum is an indicator of the inflammatory response. To prepare injured or dying cells, EL4 cells were exposed to heat shock treatment for 10 minutes followed by incubation at 37° C. for 7 hours prior to injection into animals. C57BL/6 mice were injected peritoneally with dying EL4 cells alone, dying EL4 cells coinjected with 10 µg uricase (which eliminates uric acid), as well as PBS alone, uricase alone, or untreated as controls. Following injection of dying cells into the animals, the EL4 cells and uricase are quickly taken up into the blood stream and an inflammatory response is mounted. To monitor the level of the resulting inflammatory response, peritoneal fluid was harvested 17 hours after injection and the amount of neutrophils present was measured by flow cytometry using an antibody (7/4 Ab) that recognizes a neutrophil-specific antigen. The results are presented in FIG. 5. The data show that when uricase was co-injected with dead cells, the resulting inflammation was markedly inhibited. These results indicate that MSU crystals play a key role in inflammation in response to injured or dying cells. The results further indicate that inflammation may be reduced by the administration of substances that reduce the concentration of uric acid in vivo.

Example VIII

Xanthine Crystals Rapidly Activate Dendritic Cells

Figure 6:
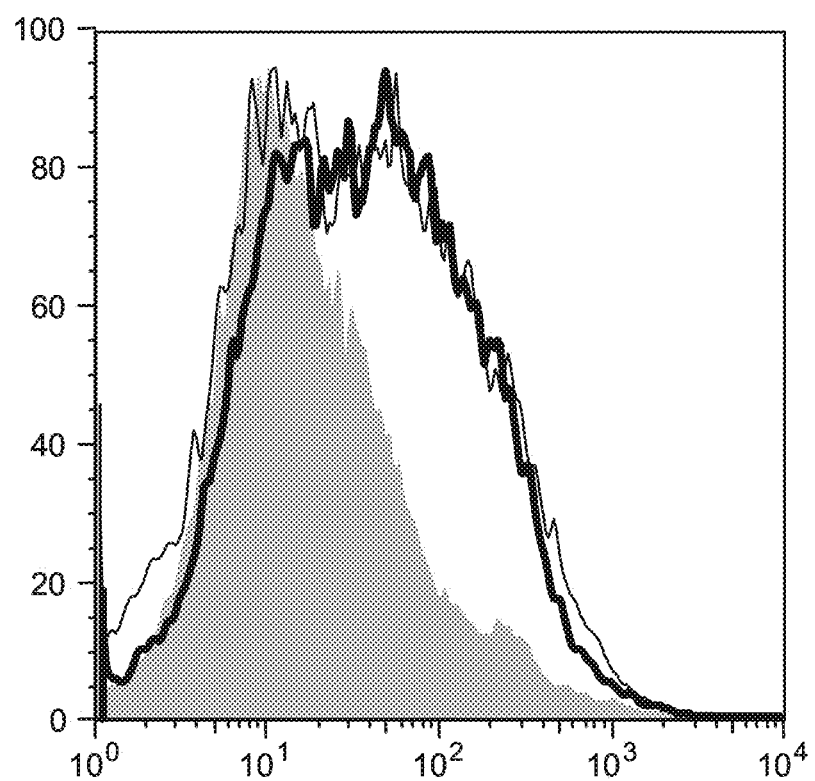
FIG. 6 is a graph depicting expression of CD86 on dendritic cells following exposure to xanthine crystals or MSU crystals and demonstrating that xanthine crystals rapidly activate dendritic cells in vitro as efficiently as MSU crystals. Bone marrow-derived dendritic cells from Balb/c mice were untreated (shaded area) or incubated with 300 μg/ml of pre-formed MSU crystals (thin line) or xanthine crystals (thick line) for 6 hours. The expression of CD86 on CD11c+ cells was then analyzed by flow cytometry.

Based upon the results set forth in Examples I-VI which identify MSU crystals as having adjuvant activity, it was concluded that other crystals with similar properties should display djuvant activity. Accordingly, the effect of xanthine crystals on expression of costimulators on cultured dendritic cells was tested in experiments similar to those described in Example V above. Xanthine was added to cultures of primary bone-marrow derived dendritic cells. Specifically, bone marrow-derived dendritic cells from Balb/c mice in 6 well plates were untreated (shaded area) or incubated with pre-formed xanthine crystals at 300 μg/ml final concentration (thick line), or with preformed MSU crystals at 300 μg/ml final concentration (thin line) for 6 hours. The expression of CD86 on CD11c+ cells was then analyzed by flow cytometry. Antibody staining of untreated cells was not significantly higher than that of background where no antibody was employed. As shown in FIG. 6, xanthine stimulated the dendritic cells to increase their expression of CD86 markedly within six hours of xanthine addition, and to a similar extent as did MSU crystals.

Example IX

Xanthine Crystals Provide Adjuvant Activity

To further evaluate the activity of xanthine crystals, xanthine crystals were tested for adjuvant activity in experiments carried out similarly to those described in Example II above. Highly purified uric acid (500 μg), highly purified xanthine (500 μg), or PBS as control were mixed with 2 μg gp120/latex beads in 100 μl of saline and injected into two Balb/c mice. CTL from these mice were assayed for killing of 15.12 (gp120-transfected 3T3) cells (filled squares). Results from individual mice are presented (FIG. 6A-C), wherein % Lysis indicates the degree of cell killing and the E:T ratio indicates the ratio of Effector cell:Target cell, e.g., the ratio of cytotoxic T-cell:antigen presenting cell. When injected into Balb/c mice with particulate HIV gp120, xanthine crystals enhanced CTL priming to a similar degree as the MSU crystals (FIGS. 7A-C). These results demonstrate that xanthine crystals, like MSU crystals, possess adjuvant activity.

Discussion of Examples I-IX

In hyperuricemia, crystals can precipitate in joints where they cause gout, in tissues creating tophi, and/or in kidneys causing nephritis.[17,18] In these situations, the monosodium urate crystals bind to monocytes, macrophages, and epithelial cells and are thought to activate them by crosslinking cell surface receptors, possibly nonspecifically, and thereby stimulating an inflammatory reaction.[19-21] The present findings indicate that it is likely that dendritic cells are stimulated in a similar fashion and that the activation of several of these cells of the innate immune system contribute to the adjuvant effect of uric acid. The present findings also raise the possibility that dendritic cells play a role in the pathogenesis of gouty arthritis.

These findings have several possible implications for health and disease. Up until now, MSU crystals have been viewed solely as pathogenic and the biological response to them as pathological. The results of the present study suggest that the formation of these crystals and the ensuing host response could serve an important biological role in immune surveillance and the generation of adaptive immunity. In addition, it is well known that in vivo dying tissue initially provokes a strong inflammatory response but loses this phlogistic quality as it is depleted of its as yet unidentified proinflammatory mediators.[22] The present results raise the possibility that uric acid is one of the mediators that leads to the inflammatory response to injured and dying tissues. Thus, MSU could also play a role in inflammation and the innate immune response to injury.

In terms of immune surveillance, the present data lead to a model where dying cells release uric acid together with their cellular antigens (and viral antigens if present). Since mammals already have high levels of uric acid in the extracellular fluids (40-60 μg/ml), the local environment around the dying cells becomes supersaturated with uric acid leading to the formation of crystals of monosodium uric acid. Elevation in local uric acid levels should be even more in higher primates, including man, because they lack uricase activity. Dendritic cells will ingest the cellular debris and thereby acquire antigens from the dying cells. At the same time they will receive a "danger signal" from the uric acid (and the HMW endogenous adjuvant) and be stimulated to mature and become immunostimulatory. MSU crystals are also known to stimulate monocytes and epithelial cells to produce cytokines and chemokines that may further potentiate this process.[18] Thus, uric acid alerts the immune system to cell death which is a hallmark of potential danger to the host. If the dying cell contains antigens to which the host is not tolerant, then an immune response will be stimulated. Thus, this provides a mechanism for the immune system to generate responses against tumors and viral infections that lack adjuvants.

In the same way, the danger signal provided by uric acid and other endogenous adjuvants could underlie the initiation of autoimmunity in genetically susceptible individuals. In this context it is interesting that patients with certain autoimmune diseases have been reported to have a higher incidence of hyperuricemia than controls.[17,23]

Prior to the present invention, a need existed for the development of additional and more effective adjuvants for use in man. Alum, the principal adjuvant approved for use in man, is relatively weak, does not generally elicit CD8 immunity, and may preferentially induce TH2-biased responses. As shown herein, uric acid represents a novel class of adjuvant distinct from those of microbial origin. It stimulates strong CD8 T cell immunity. Since it is a normal component of the host, its local administration should be relatively safe. Therefore, the present findings indicate that uric acid and other crystalline molecules with like characteristics are useful as a class of adjuvant for vaccines.

The features and other details of the invention, either as steps of the invention or as combinations of parts of the invention, will now be more particularly described and pointed out in the claims. It will be understood that the particular embodiments of the invention are shown by way of illustration and not as limitations of the invention. The principle features of this invention can be employed in various embodiments without departing from the scope of the invention.

Cited References

1. Bancherau, J. & Steinman, R. M. Dendritic cells and the control of immunity. *Nature* 392, 245-52 (1998).

2. Hunter, R. L. Overview of vaccine adjuvants: present and future. *Vaccine* 20 Suppl 3, S7-12. (2002).
3. Janeway, C. A., Jr. Approaching the asymptote? Evolution and revolution in immunology. *Cold Spring Harb Symp Quant Biol* 54, 1-13 (1989).
4. Banchereau, J. et al. Immunobiology of dendritic cells. *Annu Rev Immunol* 18, 767-811 (2000).
5. Cox, J. C. & Coulter, A. R. Adjuvants—a classification and review of their modes of action. *Vaccine* 15, 248-56. (1997).
6. Schijns, V. E. Immunological concepts of vaccine adjuvant activity. *Curr Opin Immunol* 12, 456-63. (2000).
7. Medzhitov, R. & Janeway, C., Jr. Innate immune recognition: mechanisms and pathways. *Immunol Rev* 173, 89-97 (2000).
8. Kaisho, T. & Akira, S. Toll-like receptors as adjuvant receptors. *Biochim Biophys Acta* 1589, 1-13. (2002).
9. Van Parijs, L. & Abbas, A. K. Homeostasis and self-tolerance in the immune system: turning lymphocytes off. *Science* 280, 243-8. (1998).
10. Matzinger, P. Tolerance, danger, and the extended family. *Annu Rev Immunol* 12, 991-1045 (1994).
11. Janeway, C. A., Jr. The immune system evolved to discriminate infectious nonself from noninfectious self. *Immunol Today* 13, 11-6 (1992).
12. Matzinger, P. An innate sense of danger. *Semin Immunol* 10, 399-415 (1998).
13. Albert, M. L., Sauter, B. & Bhardwaj, N. Dendritic cells acquire antigen from apoptotic cells and induce class I-restricted CTLs. *Nature* 392, 86-9 (1998).
14. Gallucci, S., Lolkema, M. & Matzinger, P. Natural adjuvants: endogenous activators of dendritic cells. *Nat Med* 5, 1249-55 (1999).
15. Shi, Y. & Rock, K. L. Cell death releases endogenous adjuvants that selectively enhance immune surveillance of particulate antigens. *Eur J Immunol* 32, 155-62. (2002).
16. Shi, Y., Zheng, W. & Rock, K. L. Cell injury releases endogenous adjuvants that stimulate cytotoxic T cell responses. *Proc Natl Acad Sci USA* (2000).
17. Talbott, J. H. & Yu, T.-F. *Gout and uric acid metabolism* (Stratton Intercontinental Medical Book Corp., New York, 1976).
18. Smyth, C. J. & Holers, V. M. *Gout, Hyperuricemia, and Other Crystal-Associated Arthropathies* (Marcel Dekker, New York, 1998).
19. Yagnik, D. R. et al. Noninflammatory phagocytosis of monosodium urate monohydrate crystals by mouse macrophages. Implications for the control of joint inflammation in gout. *Arthritis Rheum* 43, 1779-89. (2000).
20. Landis, R. C. et al. Safe disposal of inflammatory monosodium urate monohydrate crystals by differentiated macrophages. *Arthritis Rheum* 46, 3026-33. (2002).
21. Koka, R. M., Huang, E. & Lieske, J. C. Adhesion of uric acid crystals to the surface of renal epithelial cells. *Am J Physiol Renal Physiol* 278, F989-98. (2000).
22. Majno, G. & Joris, I. *Cells, Tissues, and Disease: Principles of General Pathology* (Blackwell Science Inc, 1996).
23. Bosmansky, K. & Trnaysky, K. [Serum uric acid levels in disorders of the rheumatic type]. *Z Rheumatol* 43, 59-62. (1984).
24. Coligan, J. E., Kruisbeek, A. M., Margulies, D. H., Shevach, E. M. & Strober, W. *Current Protocols in Immunology* (Jon Wiley & Sons, Hoboken, N.J., 1991).

What is claimed is:

1. A method of eliciting an antigen-specific immune response in a subject, comprising administering purified uric acid and an antigen in an amount sufficient to elicit said antigen-specific immune response.

2. A method according to claim 1, wherein the antigen is selected from the group consisting of one or more of a viral antigen, a tumor antigen, a bacterial antigen, a parasitic antigen, a pathogenic self protein, a protein, a peptide, a carbohydrate, a lipid, a nucleic acid, an inactivated virus and an inactivated bacteria.

3. A method of activating an antigen-presenting cell, comprising contacting said antigen-presenting cell with an effective amount of purified uric acid and an effective amount of an antigen, such that the antigen-presenting cell is activated.

4. A method of inducing in a subject at risk of exposure to a pathogen an increased non-specific resistance to the pathogen, comprising administering a purified uric acid in an amount sufficient to increase said non-specific resistance.

5. A method according to claim 1, wherein the antigen is a viral antigen.

6. A method according to claim 1, wherein the antigen is a tumor antigen.

7. A method according to claim 1, wherein the antigen is a bacterial antigen.

8. A method according to claim 1, wherein the antigen is a parasitic antigen.

9. A method according to claim 1, wherein the antigen is a pathogenic self protein.

10. A method according to claim 1, wherein the antigen is selected from the group consisting of protein, peptide, carbohydrate, lipid, and nucleic acid.

11. A method according to claim 1, wherein the antigen is inactivated virus or bacteria.

12. A method according to claim 1, wherein the antigen comprises a peptide.

13. A method according to claim 1, wherein the antigen comprises a mixture of peptides.

14. A method according to claim 13, wherein the peptides comprise a mixture of peptide epitopes derived from the antigenic proteins of a pathogenic organism.

15. A method according to claim 1, wherein the uric acid is present in an amount sufficient to precipitate in vivo.

16. A method according to claim 1, wherein the uric acid is in the form of monosodium urate crystals.

\* \* \* \* \*

SEQUENCE LISTING

```
<160> NUMBER OF SEQ ID NOS: 2

<210> SEQ ID NO 1
<211> LENGTH: 10
<212> TYPE: PRT
<213> ORGANISM: HIV Virus

<400> SEQUENCE: 1

Arg Gly Pro Gly Arg Ala Phe Val Thr Leu
1               5                   10

<210> SEQ ID NO 2
<211> LENGTH: 8
<212> TYPE: PRT
<213> ORGANISM: HIV Virus

<400> SEQUENCE: 2

Ser Ile Ile Asn Phe Glu Lys Leu
1               5
```